United States Patent
Gutierrez et al.

(10) Patent No.: US 11,338,040 B2
(45) Date of Patent: May 24, 2022

(54) IMMUNOMODULATORY COMPOUNDS

(71) Applicant: Leidos, Inc., Reston, VA (US)

(72) Inventors: Gabriel M. Gutierrez, Reston, VA (US); James Pannucci, Reston, VA (US); Vinayaka Kotraiah, Reston, VA (US); Timothy W. Phares, Reston, VA (US); Cecille D. Browne, Reston, VA (US)

(73) Assignee: Leidos, Inc., Reston, VA (US)

( * ) Notice: Subject to any disclaimer, the term of this patent is extended or adjusted under 35 U.S.C. 154(b) by 0 days.

(21) Appl. No.: 17/337,489

(22) Filed: Jun. 3, 2021

(65) Prior Publication Data

US 2021/0379189 A1   Dec. 9, 2021

Related U.S. Application Data

(60) Provisional application No. 63/034,554, filed on Jun. 4, 2020.

(51) Int. Cl.
| | | |
|---|---|---|
| *A61K 38/10* | (2006.01) | |
| *C07K 7/08* | (2006.01) | |
| *A61K 47/62* | (2017.01) | |
| *A61K 47/60* | (2017.01) | |

(52) U.S. Cl.
CPC .............. *A61K 47/62* (2017.08); *A61K 38/10* (2013.01); *A61K 47/60* (2017.08); *C07K 7/08* (2013.01)

(58) Field of Classification Search
CPC .................................. A61K 38/10; C07K 7/08
See application file for complete search history.

(56) References Cited

U.S. PATENT DOCUMENTS

| | | | |
|---|---|---|---|
| 10,098,950 B2 | 10/2018 | Gutierrez et al. | |
| 10,799,555 B2 | 10/2020 | Gutierrez et al. | |
| 10,799,581 B2 | 10/2020 | Gutierrez et al. | |
| 11,033,622 B2 | 6/2021 | Gutierrez et al. | |
| 2002/0111323 A1 | 8/2002 | Martin et al. | |
| 2011/0203015 A1 | 8/2011 | Sampson et al. | |
| 2011/0318373 A1 | 12/2011 | Sasikumar et al. | |
| 2013/0017403 A1 | 1/2013 | Huang et al. | |
| 2013/0237580 A1 | 9/2013 | Sasikumar et al. | |
| 2015/0125955 A1 | 5/2015 | Chomont et al. | |
| 2016/0130345 A1 | 5/2016 | Fotin-Mleczek et al. | |
| 2017/0182150 A1 | 6/2017 | Kallen et al. | |
| 2017/0274074 A1 | 9/2017 | Das-Young et al. | |
| 2018/0339044 A1* | 11/2018 | Gutierrez ........... | C07K 16/2818 |

FOREIGN PATENT DOCUMENTS

| | | |
|---|---|---|
| CN | 105504018 A | 4/2016 |
| CN | 107383174 A | 11/2017 |
| WO | 9842752 A1 | 10/1998 |
| WO | 2012168944 A1 | 12/2012 |
| WO | 2013144704 A1 | 10/2013 |
| WO | 2014127917 A1 | 8/2014 |
| WO | 2014209804 A1 | 12/2014 |
| WO | 2016028672 A1 | 2/2016 |
| WO | 2016061133 A1 | 4/2016 |
| WO | 2017023753 A1 | 2/2017 |
| WO | 2017062888 A1 | 4/2017 |
| WO | 2018053218 A1 | 3/2018 |
| WO | 2018218137 A1 | 11/2018 |

OTHER PUBLICATIONS

PCTUS2020033996 International Search Report and Written Opinion, dated Sep. 17, 2020.
Penchala et al., "A biomimetic approach for enhancing the in vivo half-life of peptides," Nat. Chem. Biol. 11, 793-98, 2015.
Peptide Atlas searches, SEQ ID No. 1, 2 pages, Oct. 1, 2020.
Peptide Atlas searches, SEQ ID No. 8, 2 pages, Oct. 7, 2020.
Phares et al., "Enhancement of the immune response to plasmodium yoelii circumsporozoite protein by PD-1 inhibitors," Amer. J. Tropical Med. and Hygiene 97, Abstract No. 1062, Nov. 1, 2017, 1 page.
Rivera et al., "Hair Repigmentation During Immunotherapy Treatment With an Anti-Programmed Cell Death 1 and Anti-Programmed Cell Death Ligand 1 Agent for Lung Cancer," JAMA Dermatol. Jul. 12, 2017. doi: 10.1001/jamadermatol.2017.2106, Jul. 12, 2017.
Sharma & Allison, "Immune Checkpoint Targeting in Cancer Therapy: Toward Combination Strategies with Curative Potential," Cell 161, 205-14, 2015.
Shindo et al., "Combination Immunotherapy with 4-1BB Activation and PD-1 Blockade Enhances Antitumor Efficacy in a Mouse Model of Subcutaneous Tumor," Anticancer Res. 35, 129-36, 2015.
Skalniak et al., "Small-molecule inhibitors of PD-1/PD-L1 immune checkpoint alleviate the PD-L1-induced exhaustion of T-cells," Oncotarget, Advance Publications, Aug. 7, 2017, 15 pages.
Smith, "Pigmented skin lesions lightened during melanoma immunotherapy," http://www.mdedge.com/edermatologynews/article/132598/melanoma/pigmented-skin-lesions-lightened-during-melanoma, Mar. 2, 2017.
Tzeng et al., "PD-1 blockage reverses immune dysfunction and hepatitis B viral persistence in a mouse animal model," PLoS One 7(6):e39179, 2012.
Van Dessel et al., "Potent and tumor specific: arming bacteria with therapeutic proteins," Ther. Deliv. 6, 385-99, 2015.
Wang et al., "Fibrinogen-like Protein 1 is a Major Immune Inhibitory Ligand of LAG-3," Cell 176, 334-47, Jan. 10, 2019.
Yang et al., "Oral vaccination with *Salmonella* simultaneously expressing Yersinia pestis F1 and V antigens protects against bubonic and pneumonic plague," J Immunol. 178, 1059-67, 2007.

(Continued)

*Primary Examiner* — Lianko G Garyu

(74) *Attorney, Agent, or Firm* — Banner & Witcoff, Ltd.

(57) ABSTRACT

This disclosure provides peptide conjugates that are useful for inhibiting the progression of a hyperproliferative disorder, inhibiting the progression of sepsis, inhibiting the progression of an infectious disease, enhancing a response to a vaccine, or inhibiting the progression of a synucleinopathy.

16 Claims, 10 Drawing Sheets

Specification includes a Sequence Listing.

(56) References Cited

OTHER PUBLICATIONS

Ye et al., "T-cell exhaustion in chronic hepatitis B infection: current knowledge and clinical significance," Cell Death Dis. Mar. 2019;6:e1694, 2015.
Young et al., "Co-inhibition of CD73 and A2AR Adenosine Signaling Improves Anti-tumor Immune Responses," Cancel Cell 30, 391-403, 2016.
Zarganes-Tzitzikas et al., "Inhibitors of programmed cell death 1 (PD-1): a patent review," Expert Opinion on Therapeutic Patents 26, 973-77, published on-line Jul. 6, 2016.
Zhan et al., "From monoclonal antibodies to small molecules: the development of inhibitors targeting the PD-1/PD-L1 pathway," Drug Discovery Today 21, 1027-36, Jun. 2016.
International Search Report and Written Opinion—International Patent Application No. PCT/US2021/054127, dated Oct. 8, 2021 (29 pages).
Yayi He et al., "Lymphocyte-activation gene-3, an important immune checkpoint in cancer", Cancer Science, vol. 107, No. 9, Aug. 25, 2016, pp. 1193-1197.
Adams et al., "Big opportunities for small molecules in immuno-oncology," Nature Reviews Drug Discovery Advance Online Publication, Jul. 31, 2016, 20 pages.
Andrews et al., "LAG3 (CD223) as a Cancer Immunotherapy Target," Immunol. Rev. 276, 80-96, 2017.
Bruno et al., "Basics and recent advances in peptide and protein drug delivery," Ther. Deliv. 4, 1443-67, 2013.
Bu et al., "Learning from PD-1 Resistance: New Combination Strategies," Trends Mol. Med. 22, 448-51, 2016.
Burnett & Rossi, "RNA-based Therapeutics—Current Progress and Future Prospects," Chem Biol. 19, 60-71, 2012.
Cao, "Advances in Delivering Protein and Peptide Therapeutics," Pharmaceutical Technology 40, 22-24, Nov. 2, 2016.
Chang et al., "Blocking of the PD-1/PD-L1 Interaction by a D-Peptide Antagonist for Cancer Immunotherapy," Angew. Chem. Int. Ed. 54, 11760-64, 2015.
Cherkassky et al., "Human CAR T cells with cell-intrinsic PD-1 checkpoint blockade resist tumor-mediated inhibition," J. Clin. Invest. 126, 3130-44, 2016.
Chong et al., "PD-1 blockade modulates chimeric antigen receptor (CAR)-modified T cells: refueling the CAR," Blood. 129(8), 1039-41, 2017, published on-line Dec. 28, 2016.
Creative Biolabs User Manual, "TriCo-20TM Phage Display 20-mer Random Peptide Library," 14 pages, Aug. 4, 2009.
Differding, "AUNP-12—A Novel Peptide Therapeutic Targeting PD-1 Immune Checkpoint Pathway for Cancer Immunotherapy—Structure Activity Relationships & Peptide/Peptidomimetic Analogs," available at http://www.differding.com/data/AUNP_12_A_novel_peptide_therapeutic_targeting_PD_1_immune_checkpoint_pathway_for_cancer_immunotherapy.pdf, Feb. 26, 2014.
Duraiswamy et al., "Dual Blockade of PD-1 and CTLA-4 Combined with Tumor Vaccine Effectively Restores T-Cell Rejection Function in Tumors," Cancer Res. 73, 3591-603, 2013.
Feridooni et al., "Noninvasive Strategies for Systemic Delivery of Therapeutic Proteins—Prospects and Challenges," Chapter 8 of Sezer, ed., Smart Drug Delivery System, available at http://www.intechopen.com/books/smart-drug-delivery-system, Feb. 10, 2016.
Gutierrez et al., International Search Report and Written Opinion for PCT/US2015/051697, 5 pages, searched Nov. 13, 2017, dated Dec. 1, 2017.
Gutierrez et al., PCT/US2015/051697 filed Sep. 15, 2017, 49 pages.
Gutierrez et al., U.S. Appl. No. 15/906,481 continuation-in-part application of U.S. Appl. No. 15/705,333, filed Feb. 27, 2018, 63 pages.
Gutierrez et al., U.S. Appl. No. 15/906,481, Notice of Allowance dated Jun. 9, 2020, 8 pages.
Gutierrez et al., U.S. Appl. No. 15/906,481, Response to Restriction Requirement filed May 26, 2020, 5 pages.
Gutierrez et al., U.S. Appl. No. 15/908,861 divisional application of U.S. Appl. No. 15/705,333, filed Mar. 1, 2018, 49 pages.
Gutierrez et al., U.S. Appl. No. 15/908,861, Notice of Allowance dated Jun. 12, 2020, 8 pages.
Gutierrez et al., U.S. Appl. No. 15/908,861, Response to Restriction Requirement filed May 26, 2020, 5 pages.
Gutierrez et al., U.S. Appl. No. 16/879,884 Final Office Action dated Nov. 30, 2021.
Gutierrez et al., U.S. Appl. No. 16/879,884 Nonfinal Office Action dated Jul. 21, 2021.
Gutierrez et al., U.S. Appl. No. 16/879,884 Reponse to Restriction Requirement filed Jun. 15, 2021.
Gutierrez et al., U.S. Appl. No. 16/879,884 Response to Final Office Action filed Feb. 28, 2022.
Gutierrez et al., U.S. Appl. No. 16/879,884 Response to Nonfinal Office Action filed Oct. 21, 2021.
Gutierrez et al., U.S. Appl. No. 16/879,884 Restriction Requirement dated May 17, 2021.
Gutierrez et al., U.S. Appl. No. 17/015,658, filed Sep. 9, 2020.
Gutierrez et al., U.S. Appl. No. 17/026,447, filed Sep. 21, 2020, 49 pages.
Gutierrez et al., U.S. Appl. No. 17/317,985, filed May 12, 2021.
Gutierrez et al., U.S. Appl. No. 17/386,637, filed Jul. 28, 2021.
Gutierrez et al., U.S. Appl. No. 17/386,637 Preliminary Amendment filed Jul. 28, 2021.
Gutierrez et al., U.S. Appl. No. 17/497,069, filed Oct. 8, 2021.
International Search Report and Written Opinion for PCT/US2018/020209, dated Oct. 22, 2018, 17 pages.
International Search Report and Written Opinion for PCT/US2018/034625, dated Sep. 6, 2018, 15 pages.
International Search Report and Written Opinion of the International Searching Authority for International Patent Application No. PCT/US2020/03996, dated Sep. 17, 2020 (18 pages).
International Search Report of the International Searching Authority and Invitation to Pay Additional Fees for International Patent Application No. PCT/US2020/03996, dated Jul. 27, 2020 (14 pages).
John et al., "Blockade of PD-1 immunosuppression boosts CAR T-cell therapy," Oncolmmunology 2, e26286, 3 pages, 2013.
Kaczmarek et al., "Advances in the delivery of RNA therapeutics: from concept to clinical reality," Genome Medicine 2017; 9:60, 16 pages.
Kavikansky & Pavlick, "Beyond Checkpoint Inhibitors: The Next Generation of Immunotherapy in Oncology," Amer. J. Hematol. Oncol. 13, 9-20, 2017.
Kontermann, "Half-life extended biotherapeutics," Expert Opin. Biol. Ther. 16, 903-15, 2016.
Li et al., "Discovery of peptide inhibitors targeting human programmed death 1 (PD-1) receptor," Oncotarget 7, 64967-76, Aug. 12, 2016.
Lichtenegger et al., "Targeting LAG-3 and PD-1 to Enhance T Cell Activation by Antigen-Presenting Cells," Frontiers in Immunology 9, Article 385, Feb. 2018.
Magiera-Mularz et al., "Bioactive macrocyclic inhibitors of the PD-1/PD-L1 immune checkpoint," Angewandte Chemie Int. Ed. 10.1002/anie.201707707, e-published Sep. 26, 2017.
Mao et al., "Pathological synuclein transmittion initiated by binding lymphocyte-activation gene 3," Science 353, Sep. 2016.
Maute et al., "Engineering high-affinity PD-1 variants for optimized immunotherapy and immuno-PET imaging," Proc. Natl. Acad. Sci. USA, E6506-E6514, published online Nov. 10, 2015.
Morrissey et al., "Immunotherapy and Novel Combinations in Oncology: Current Landscape, Challenges, and Opportunities," Clinical and Translational Science 9, 89-104, 2016.
Patel et al., "Recent Advances in Protein and Peptide Drug Delivery: A Special Emphasis on Polymeric Nanoparticles," Protein. Pept. Lett. 21, 1102-20, 2014.
Patil et al., "Targeting Immune Cell Checkpoints during Sepsis," Int. J. Mol. Sci. 18, 24 pages, 2017.
PCTUS2020033996 International Search Report and Invitation to Pay Additional Fees, dated Jul. 27, 2020.
Gutierrez et al., Notice of Allowance dated Mar. 28, 2022 in U.S. Appl. No. 16/879,884, filed May 21, 2020.

(56) References Cited

OTHER PUBLICATIONS

Gutierrez et al., Allowed Claims, dated Mar. 28, 2822 in U.S. Appl. No. 16/879,884, filed May 21, 2020.

* cited by examiner

IMMUNOMODULATORY COMPOUNDS

This application incorporates by reference the contents of a 2.65 kb text filed created on Jun. 1, 2020 and named "00047900275 sequencelisting.txt," which is the sequence listing for this application.

Each scientific reference, patent, and published patent application cited in this disclosure is incorporated herein by reference in its entirety.

TECHNICAL FIELD

This disclosure relates generally to immunomodulatory peptides.

BACKGROUND

There is a continuing need for useful modulators of immune checkpoint pathways. For example, programmed cell death-1 (PD1) and its ligands, PD-L1 and PD-L2, are widely expressed and exert a number of immunoregulatory roles in T cell activation, including attenuation of immunity against tumor cells and infectious agents. PD1 is therefore an attractive target for a variety of therapeutic applications. Cytotoxic T-lymphocyte-associated antigen (CTLA-4) provides a negative signal to T cells and is also an attractive therapeutic target.

Lymphocyte activation gene 3 (LAG3, also known as LAG-3, LAG 3, Lag3, CD223, FDC protein) is a member of the immunoglobulin superfamily of receptors. LAG3 is expressed on immune cells (activated T cells, Huard et al., 1994; natural killer cells, Triebel et al., 1990; B cells, Kisielow et al., 2005; plasmacytoid dendritic cells, Workman et al., 2009), where it binds to MHC class II (MHC-II) and serves as an immune checkpoint receptor. LAG3 also binds to fibrinogen-like protein (FGL1), and disrupting this binding can potentiate anti-tumor immunity (Wang et al., 2019).

LAG3 is also expressed on neurons, where it serves as a receptor for the α-synuclein aggregates characteristic of synucleinopathies (Mao et al., 2016). Synucleinopathies are disorders characterized by the abnormal accumulation of aggregates of α-synuclein protein in neurons, nerve fibers, or glial cells. Synucleinopathies include idiopathic and inherited forms of Parkinson's disease (PD); Diffuse Lewy Body (DLB) disease, also known as Dementia with Lewy Bodies or Lewy body dementia; incidental Lewy body disease; Lewy body variant of Alzheimer's disease (LBV); Combined Alzheimer's and Parkinson disease (CAPD); pure autonomic failure (PAF); multiple system atrophy (MSA), such as olivopontocerebellar atrophy, striatonigral degeneration, and Shy-Drager Syndrome; pantothenate kinase-associated neurodegeneration; Down's Syndrome; Gaucher disease-related synucleinopathies; and neurodegeneration with brain iron accumulation.

DETAILED DESCRIPTION

Figure 1:
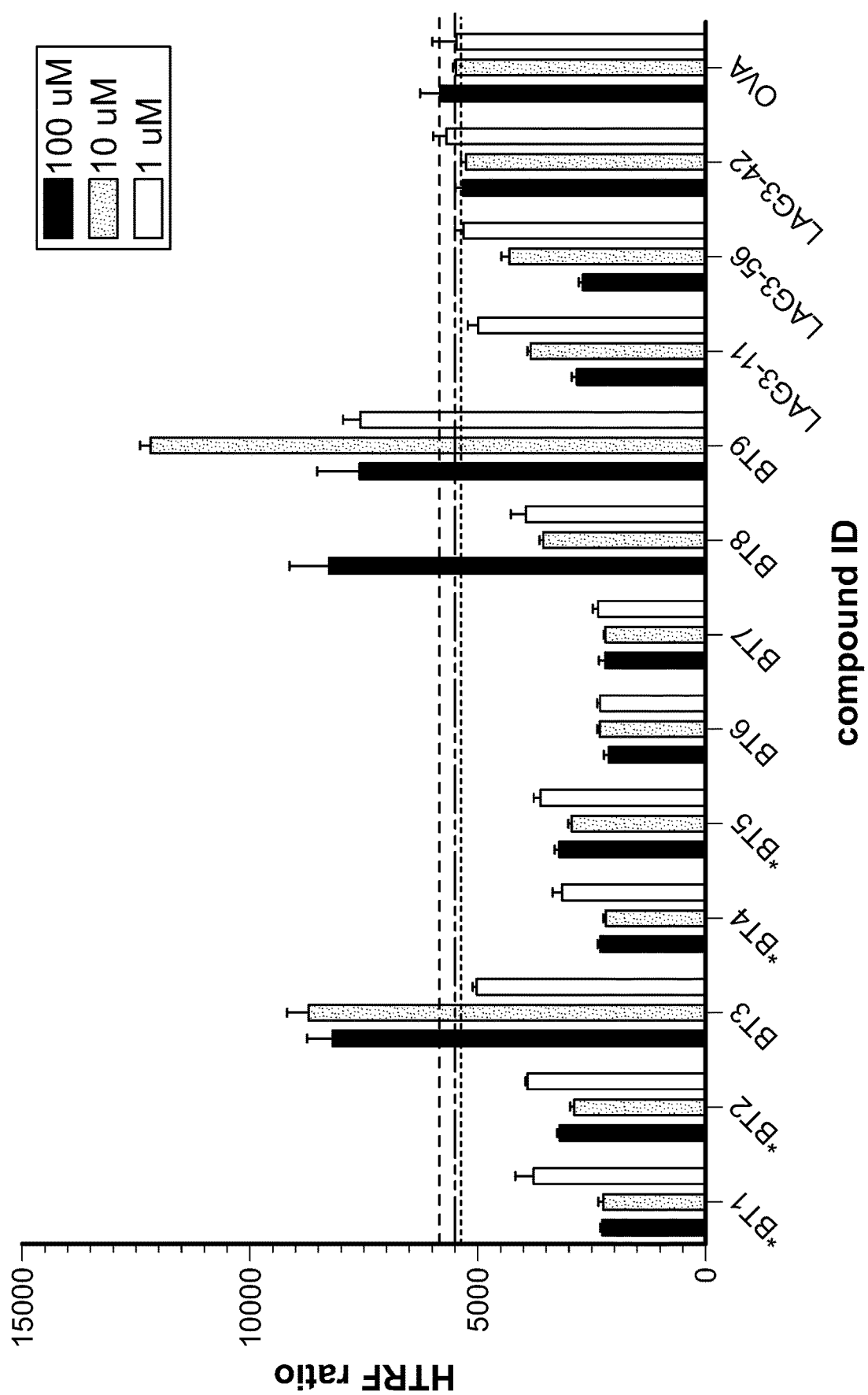
FIG. 1 is a graph reporting the results of a TR-FRET assay testing the ability of peptide conjugates and individual peptides to affect the interaction between LAG3 and MHC-II. * indicates precipitation when diluted in assay buffer at 1 mM (100 µM final).

This disclosure provides peptide conjugates that inhibit the function of PD1 and/or block the interaction of LAG3 with MHC-II. The disclosed peptide conjugates contain two peptides separated by a polyethylene glycol (PEG) linker. Each of the peptide conjugates disclosed in this specification contains two of four peptides, with the sequences and orientations as shown in Table 1.

TABLE 1

| peptide | orientation | amino acid sequence | SEQ ID NO: |
|---------|-------------|---------------------|------------|
| LD10 | forward (→) | STGQISTLRVNITAPLSQ | 1 |
| LD10 | reverse (←) | QSLPATINVRLTSIQGTS | 2 |
| LG11 | forward (→) | SAPWEPLHWPEDWWQGTGEW | 3 |
| LG11 | reverse (←) | WEGTGQWWDEPWHLPEWPAS | 4 |

"LD10" (SEQ ID NO:1) is a peptide that inhibits the function of the checkpoint receptor "programmed death 1" (PD1). "LG11" (also known as "LAG3-11") (SEQ ID NO:3) is a peptide that binds to LAG3 and blocks its interaction with MHC-II.

Examples of peptide conjugates are shown in Table 2, in which a lower case letter indicates the D form of the amino acid; "PEG$_4$" is a PEG linker of 4 PEG units, and "Ac" is C-terminal acetylation.

TABLE 2

Structure of Peptide Conjugates BT1-BT11

| | | LD10 | LG11 | LD10 |
|---|---|---|---|---|
| BT1 | H₂N-(dS)TGQISTLRVNITAPLSQ¹-PEG₄-SAPWEPLHWPEDWWQGTGEW³-amide | | → | → |
| BT2 | H₂N-SAPWEPLHWPEDWWQGTGEW³-PEG₄-(dS)TGQISTLRVNITAPLSQ¹-amide | | → | → |
| BT3 | H₂N-WEGTGQWWDEPWHLPEWPAS⁴-PEG₄-(dS)TGQISTLRVNITAPLSQ¹-amide | | ← | → |
| BT4 | H₂N-SAPWEPLHWPEDWWQGTGEW³-PEG₄-QSLPATINVRLTSIQGT(dS)²-amide | | → | ← |
| BT5 | H₂N-WEGTGQWWDEPWHLPEWPAS⁴-PEG₄-QSLPATINVRLTSIQGT(dS)²-amide | | ← | ← |
| BT6 | Ac-QSLPATINVRLTSIQGT(dS)²-PEG₄-WEGTGQWWDEPWHLPEWPAS⁴-amide | | ← | ← |
| BT7 | Ac-QSLPATINVRLTSIQGT(dS)²-PEG₄-SAPWEPLHWPEDWWQGTGEW³-amide | | ← | → |
| BT8 | H₂N-(dS)TGQISTLRVNITAPLSQ¹-PEG₄-WEGTGQWWDEPWHLPEWPAS⁴-amide | | → | ← |
| BT9 | H₂N-(dS)TGQISTLRVNITAPLSQ¹-PEG₄-(dS)TGQISTLRVNITAPLSQ¹-amide | → | | → |
| BT10 | H₂N-(dS)TGQISTLRVNITAPLSQ¹-PEG₄-QSLPATINVRLTSIQGT(dS)²-amide | → | | ← |
| BT11 | Ac-QSLPATINVRLTSIQGT(dS)²-PEG₄-QSLPATINVRLTSIQGT(dS)²-amide | ← | | ← |

[1] SEQ ID NO: 1
[2] SEQ ID NO: 2
[3] SEQ ID NO: 3
[4] SEQ ID NO: 4

As illustrated in Table 2, in some embodiments, peptides of a peptide conjugate are modified using chemical or recombinant methods to enhance stability or other pharmacokinetic properties. See, e.g., US 2017/0020956. Modifications include, but are not limited to, replacement of one or more L-amino acid with its corresponding D-form, acetylation on a C- and/or N-terminal residue, and amidation on a C- and/or N-terminal residue.

As demonstrated in the Examples below, in some cases, peptide conjugates have more potent activities than their corresponding single peptides.

In some embodiments a peptide conjugate inhibits the function of PD1. Examples of such peptide conjugates are BT7, BT9, BT10, and BT11.

In some embodiments, a peptide conjugate inhibits the interaction between LAG3 and MHC-II. Examples of such peptide conjugates are BT1, BT2, BT3, BT4, BT5, BT6, and BT7.

In some embodiments, a peptide conjugate inhibits the function of PD1 and the interaction of LAG3 and MHC-II. BT7 is an example of such a peptide conjugate.

Peptides of a peptide conjugate can be made by any method known in the art, including synthetic methods, recombinant methods, or both. Synthetic methods include solid-phase and solution methods, and may include the use of protective groups. See, e.g., Bodanszky et al. (1976), McOmie (1973), Merrifield (1963), Neurath et al. (1976), Stuart & Young (1984).

Recombinant production of the peptides used in peptide conjugates can be carried out using any nucleotide sequence(s) encoding the peptides in any suitable expression system. Nucleic acid molecules encoding one or more of the disclosed peptides can be incorporated into an expression cassette that includes control elements operably linked to the coding sequences. Control elements include, but are not limited to, initiators, promoters (including inducible, repressible, and constitutive promoters), enhancers, and polyadenylation signals. Signal sequences can be included. The expression cassette can be provided in a vector that can be introduced into an appropriate host cell for production of the peptide(s). Methods of constructing expression cassettes and expression vectors are well known. Expression vectors can include one or more expression cassettes encoding one or more peptides comprising, consisting essentially or, or consisting of any of SEQ ID NOS:1-4.

The PEG linker can be incorporated by suitable methods known in the art. In some embodiments, the linker is incorporated using FMOC chemistry. For example, the 4-mer PEG linker of BT1-BT11 was incorporated using Fmoc-N-amido-dPEG®₄-acid (Quanta BioDesign).

PEG linkers can vary in length (e.g., 2, 3, 4, 5, 6).

In some embodiments, peptide conjugates can be labeled (e.g., with biotin or a fluorescent label) and used, for example, as diagnostic reagents.

Therapeutic Uses

The peptide conjugates disclosed here have a number of therapeutic applications. "Treat," as used herein, includes reducing or inhibiting the progression of one or more symptoms of the condition for which a peptide conjugate is administered.

Peptide conjugates that inhibit the interaction between PD1 and PDL1 can be used to treat hyperproliferative disorders, including cancer, to treat infectious diseases, to enhance a response to vaccination, to treat sepsis, to promote hair re-pigmentation, and to promote lightening of a pigmented skin lesion.

Peptide conjugates that inhibit the interaction between LAG3 and MHC-II also can be used to treat hyperproliferative disorders, including cancer, and can be useful for reducing one or more symptoms of or for treating synucleopathies, infectious diseases, and sepsis and for enhancing a response to vaccination.

In some embodiments, administration is carried out in conjunction with one or more other therapies. "In conjunction with" includes administration together with, before, or after administration of the one or more other therapies.

Pharmaceutical Compositions, Routes of Administration, and Devices

One or more peptide conjugates, as discussed above, are typically administered in a pharmaceutical composition comprising a pharmaceutically acceptable vehicle. The "pharmaceutically acceptable vehicle" may comprise one or more substances which do not affect the biological activity of the peptides or modified versions thereof and, when administered to a patient, does not cause an adverse reaction. Pharmaceutical compositions may be liquid or may be lyophilized. Lyophilized compositions may be provided in a kit with a suitable liquid, typically water for injection (WFI) for use in reconstituting the composition. Other suitable forms of pharmaceutical compositions include suspensions, emulsions, and tablets.

In some embodiments, a pharmaceutical composition comprises a plurality of only one type of peptide conjugate (e.g., BT1, BT2, BT4, BT5, BT6, BT7, BT9, BT10, BT11). In other embodiments, a pharmaceutical composition comprises pluralities of more than one type of peptide conjugate (e.g., any one of BT1, BT2, BT4, BT5, BT6, BT7, BT9, BT10, BT11 and one or more of BT1, BT2, BT4, BT5, BT6, BT7, BT9, BT10, BT11).

Pharmaceutical compositions can be administered by any suitable route, including, but not limited to, intravenous, intramuscular, intradermal, intraperitoneal, subcutaneous, epidural, intratumoral, transdermal (e.g., US 2017/0281672), mucosal (e.g., intranasal or oral), pulmonary, and topical (e.g., US 2017/0274010) routes. See, e.g., US 2017/0101474.

Administration can be systemic or local. In addition to local infusions and injections, implants can be used to achieve a local administration. Examples of suitable materials include, but are not limited to, sialastic membranes, polymers, fibrous matrices, and collagen matrices.

Topical administration can be by way of a cream, ointment, lotion, transdermal patch (such as a microneedle patch), or other suitable forms well known in the art.

Administration can also be by controlled release, for example, using a microneedle patch, pump and/or suitable polymeric materials. Examples of suitable materials include, but are not limited to, poly(2-hydroxy ethyl methacrylate), poly(methyl methacrylate), poly(acrylic acid), poly(ethylene-co-vinyl acetate), poly(methacrylic acid), polyglycolides (PLG), polyanhydrides, poly(N-vinyl pyrrolidone), poly(vinyl alcohol), polyacrylamide, poly(ethylene glycol), polylactides (PLA), poly(lactide-co-glycolides) (PLGA), and polyorthoesters.

Devices comprising any of the peptide conjugates described above include, but are not limited to, syringes, pumps, transdermal patches, spray devices, vaginal rings, and pessaries.

Treatment of Hyperproliferative Disorders, Including Cancer

In some embodiments, one or more of the peptide conjugates described above are administered to a patient to inhibit the progression of a hyperproliferative disorder, including cancer. Such inhibition may include, for example, reducing proliferation of neoplastic or pre-neoplastic cells; destroying neoplastic or pre-neoplastic cells; and inhibiting metastasis or decreasing the size of a tumor.

Examples of cancers include, but are not limited to, melanoma (including cutaneous or intraocular malignant melanoma), renal cancer, prostate cancer, breast cancer, colon cancer, lung cancer, bone cancer, pancreatic cancer, skin cancer, cancer of the head or neck, uterine cancer, ovarian cancer, rectal cancer, cancer of the anal region, stomach cancer, testicular cancer, carcinoma of the fallopian tubes, carcinoma of the endometrium, carcinoma of the cervix, carcinoma of the vagina, carcinoma of the vulva, Hodgkin's Disease, non-Hodgkin's lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemias including acute myeloid leukemia, chronic myeloid leukemia, acute lymphoblastic leukemia, chronic lymphocytic leukemia, lymphocytic lymphoma, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, and T-cell lymphoma.

Combination Cancer Therapies

In some embodiments, one or more of the peptide conjugates described above are administered in conjunction with one or more other cancer therapies or immunotherapies, such as those described below.

In some embodiments, the second therapy comprises a second agent that reduces or blocks the activity of PD1 (e.g., nivolumab, pembrolizumab, durvalumab) or CTLA-4 (e.g., ipilimumab, tremelimumab).

In some embodiments, the second therapy comprises an agent that reduces or blocks the activity of PD-L1 (e.g., atezolizumab).

In some embodiments, the second therapy comprises another agent that reduces or blocks the activity of LAG3 or other inhibitory checkpoint molecules and/or molecules that suppress the immune system. These molecules include, but are not limited to:
1. V-domain Immunoglobulin Suppressor of T cell Activation (VISTA, also known as c10orf54, PD1H, DD1α, Gi24, Dies1, and SISP1; see US 2017/0334990, US 2017/0112929, Gao et al., 2017, Wang et al., 2011; Liu et al., 2015);
2. T-cell Immunoglobulin domain and Mucin domain 3 (TIM-3; see US 2017/0198041, US 2017/0029485, US 2014/0348842, Sakuishi et al., 2010);
3. killer immunoglobulin-like receptors (KIRs; see US 2015/0290316);
4. agents that inhibit indoleamine (2,3)-dioxygenase (IDO; see Mellemgaard et al., 2017);
5. B and T Lymphocyte Attenuator (BTLA; see US 2016/09222114); and
6. A2A adenosine receptor (A2AR; see Beavis et al., 2015; US 2013/0267515; US 2017/0166878; Leone et al., 2015; Mediavilla-Varela et al., 2017; Young et al., 2016).

Agents that reduce or block the activity of LAG3 include, but are not limited to, BMS-986016, IMP321, and GSK2831781 (He et al., 2016).

Agents that reduce or block the activity of VISTA include, but are not limited to, small molecules, such as CA-170, and antibodies (e.g., Le Mercier et al., 2014).

Agents that reduce or block the activity of TIM-3 include, but are not limited to, antibodies such as MBG453 and TSR-022; see Dempke et al., 2017.

Agents that reduce or block the activity of KIRs include, but are not limited to, monoclonal antibodies such as IPH2101 and Lirilumab (BMS-986015, formerly IPH2102); see Benson & Caligiuri, 2014.

Agents that reduce or block the activity of IDO include, but are not limited to, epacadostat and agents disclosed in US 2017/0037125.

Agents that reduce or block the activity of BTLA include, but are not limited to, peptides (e.g., Spodzieja et al., 2017).

Agents that reduce or block the activity of A2AR include, but are not limited to, small molecules such as CPI-444 and vipadenant.

In some embodiments, the second therapy comprises a cytokine (e.g., interleukin 7).

In some embodiments, the second therapy comprises an agonist of a stimulatory checkpoint molecule. These molecules include, but are not limited to:
1. CD40;
2. OX40;
3. glucocorticoid-induced tumor necrosis factor-related protein (GITR); and
4. Inducible T-cell COStimulator (ICOS).

Agonists of CD40 include, but are not limited to, CD40 agonist monoclonal antibodies such as cp-870,893, Chi-Lob7/4, dacetuzumab, and lucatumumab. See, e.g., Vonderheide et al., 2007; Khubchandani et al., 2009; Johnson et al., 2010; Bensinger et al., 2012; Vonderheide and Glennie, 2013; Johnson et al., 2015.

Agonists of OX40 include, but are not limited to, OX40 agonist antibodies such as MOXR0916, MED16469, MED10562, PF-045618600, GSK3174998, and INCCAGN01949, and OX40L-Fc fusion proteins, such as MEDI6383. See, e.g., Huseni et al., 2014; Linch et al., 2015; Messenheimer et al., 2017. See also Shrimali et al., 2017.

Agonists of GITR include, but are not limited to, MEDI1873. See, e.g., Schaer et al., 2012; Tigue et al., 2017.

Agonists of ICOS include, but are not limited to, ICOS agonist antibodies JTX-2011 and GSK3359609. See, e.g., Harvey et al., 2015; Michaelson et al., 2016.

In other embodiments, the second therapy comprises a 4-1BB agonist (Shindo et al., 2015), such as urelumab; a 4-1BB antagonist (see US 2017/0174773); an inhibitor of anaplastic lymphoma kinase (ALK; Wang et al., 2014; US 2017/0274074), such as crizotinib, ceritinib, alectinib, PF-06463922, NVP-TAE684, AP26113, TSR-011, X-396, CEP-37440, RXDX-101; an inhibitor of histone deacetylase (HDAC; see US 2017/0327582); a VEGFR inhibitor, such as axitinib, sunitinib, sorafenib, tivozanib, bevacizumab; and/or an anti-CD27 antibody, such as varlilumab.

In some embodiments, the second therapy comprises a cancer vaccine (e.g., Duraiswamy et al., 2013). A "cancer vaccine" is an immunogenic composition intended to elicit an immune response against a particular antigen in the individual to which the cancer vaccine is administered. A cancer vaccine typically contains a tumor antigen which is able to induce or stimulate an immune response against the tumor antigen. A "tumor antigen" is an antigen that is present on the surface of a target tumor. A tumor antigen may be a molecule which is not expressed by a non-tumor cell or may be, for example, an altered version of a molecule expressed by a non-tumor cell (e.g., a protein that is misfolded, truncated, or otherwise mutated).

In some embodiments, the second therapy comprises a chimeric antigen receptor (CAR) T cell therapy. See, e.g., John et al., 2013; Chong et al., 2016.

In some embodiments, one or more of the peptide conjugates described above are administered in conjunction with a CAR-T cell cancer therapy to increase the efficacy of the CAR-T cell cancer therapy.

In some embodiments, one or more of the peptide conjugates described above are administered in conjunction with an oncolytic virus as disclosed, for example, in US 2017/0143780. Non-limiting examples of oncolytic viruses are described above.

Additional Therapeutic Uses

Synucleinopathies

In some embodiments, one or more of the peptide conjugates described above (e.g., BT1, BT2, BT4, BT5, BT6, BT7) may be useful to reduce a symptom of a synucleinopathy, either alone or in combination with other therapeutic interventions such as L-DOPA, dopamine agonists (e.g., ropinirole, pramipexole), dopamine reuptake inhibitors (e.g., amantadine), and cholinesterase inhibitors (e.g., donepezil, rivastigmine, galantamine). Examples of synucleinopathies include idiopathic and inherited forms of Parkinson's disease (PD); Diffuse Lewy Body (DLB) disease, also known as Dementia with Lewy Bodies or Lewy body dementia; incidental Lewy body disease; Lewy body variant of Alzheimer's disease (LBV); Combined Alzheimer's and Parkinson disease (CAPD); pure autonomic failure (PAF); multiple system atrophy (MSA), such as olivopontocerebellar atrophy, striatonigral degeneration, and Shy-Drager Syndrome; pantothenate kinase-associated neurodegeneration; Down's Syndrome; Gaucher disease-related synucleinopathies; and neurodegeneration with brain iron accumulation.

Sepsis

LAG3 expression is up-regulated in sepsis (Patil et al., 2017). Accordingly, one or more of the peptide conjugates described above (e.g., BT1, BT2, BT4, BT5, BT6, BT7) may be useful to treat sepsis, either alone or in combination with other therapeutic interventions such as antibiotics, intravenous fluids, and vasopressors.

Infectious Diseases

In some embodiments, one or more of the peptide conjugates described above can be administered to treat infectious diseases, including chronic infections, caused, e.g., by viruses, fungi, bacteria, and protozoa, and helminths, either alone or in combination with other therapeutic interventions.

Examples of viral agents include human immunodeficiency virus (HIV), Epstein Barr Virus (EBV), *Herpes simplex* (HSV, including HSV1 and HSV2), Human Papillomavirus (HPV), Varicella *zoster* (VSV) Cytomegalovirus (CMV), and *hepatitis* A, B, and C viruses.

Examples of fungal agents include *Aspergillus, Candida, Coccidioides, Cryptococcus*, and *Histoplasma capsulatum*.

Examples of bacterial agents include Streptococcal bacteria (e.g., *pyogenes, agalactiae, pneumoniae*), *Chlamydia pneumoniae, Listeria monocytogenes*, and *Mycobacterium tuberculosis*.

Examples of protozoa include *Sarcodina* (e.g., *Entamoeba*), *Mastigophora* (e.g., *Giardia*), *Ciliophora* (e.g., *Balantidium*), and *Sporozoa* (e.g., *Plasmodium falciparum, Cryptosporidium*).

Examples of helminths include *Platyhelminths* (e.g., *Trematodes, cestodes*), *Acanthocephalins*, and *Nematodes*.

Vaccine Adjuvants

In some embodiments one or more of the peptide conjugates can be administered as a vaccine adjuvant in conjunction with a vaccine to enhance a response to vaccination (e.g., by increasing effector T cells and/or reducing T cell exhaustion). The vaccine can be, for example, an RNA vaccine (e.g., US 2016/0130345, US 2017/0182150), a DNA vaccine, a recombinant vector, a protein vaccine, or a peptide vaccine. Such vaccines can be delivered, for example, using virus-like particles, as is well known in the art.

Example 1. Disruption of LAG3-MHC-II Interaction

A Homogeneous Time-resolved Fluorescence (HTRF) LAG3/MHC-II binding assay (Cisbio US Inc.) was used to measure the interaction between MHC-II and LAG3 in the presence of various peptides and peptide conjugates. In this assay, the interaction between Tag1-LAG3 and Tag2-MHC-II is detected by using anti-Tag1-Terbium (HTRF donor) and anti-Tag2-XL665 (HTRF acceptor). When the donor and acceptor antibodies are brought into close proximity due to LAG3 and MHC-II binding, excitation of the donor antibody triggers fluorescent resonance energy transfer (FRET) towards the acceptor antibody, which in turn emits specifically at 665 nm. This specific signal is directly proportional to the extent of LAG3/MHC-II interaction. Thus, an agent that blocks the interaction between LAG3 and MHC-II will cause a reduction in HTRF ratio.

Each of peptide conjugates BT1, BT2, BT3, BT4, BT5, BT6, BT7, BT8, BT9, and peptides LG11 (LAG3-11), LAG3-56 (SEQ ID NO:5), and LAG3-42 (SEQ ID NO:6) was tested at 3 concentrations: 100 μM, 10 μM, and 1 μM. The results are shown in FIG. 1. The dashed-lines represent the HTRF ratio readout of a control ovalbumin peptide (OVA, SEQ ID NO:7) (baseline) at the respective concentrations.

Each concentration of peptide conjugates BT1, BT2, BT4, BT5, BT6, BT7, and two concentrations of BT8 reduced the HTRF signal in this assay. BT9 contains two LD10 (SEQ ID NO:1) peptides yet behaved in this assay like a LAG3 agonist. BT3 had similar agonistic response.

Example 2. Disruption of LAG3-MHC-II Interaction; Dilution Curves peptide conjugates and LG peptides were tested in full dilution curves in the LAG3:MHCII TR-FRET Assay described above to estimate $IC_{50}$. peptide conjugates were tested starting at 100 μM or 10 μM. LG peptides were tested starting at 100 μM. The results are shown in FIGS. 2A-9B.

Figures 2A, 2B:
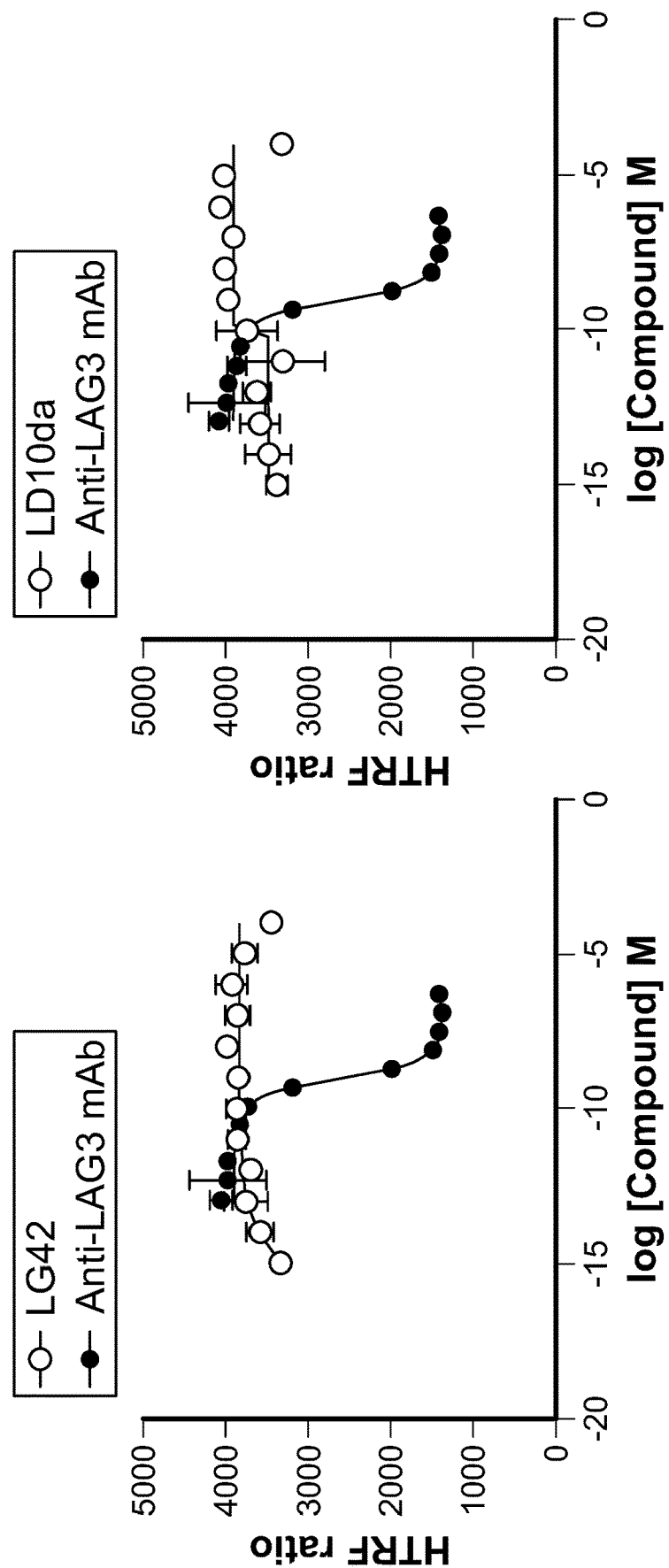
FIG. 2A is a graph showing the results of a TR-FRET assay testing peptide LG42 (SEQ ID NO:6).
FIG. 2B is a graph showing the results of a TR-FRET assay testing peptide LD10da (SEQ ID NO:8).

Peptides LG42 (LAG3-42; SEQ ID NO:6) and LD10da (SEQ ID NO:8) showed no response in this assay, confirming previous observations (FIG. 2A and FIG. 2B).

Figure 3:
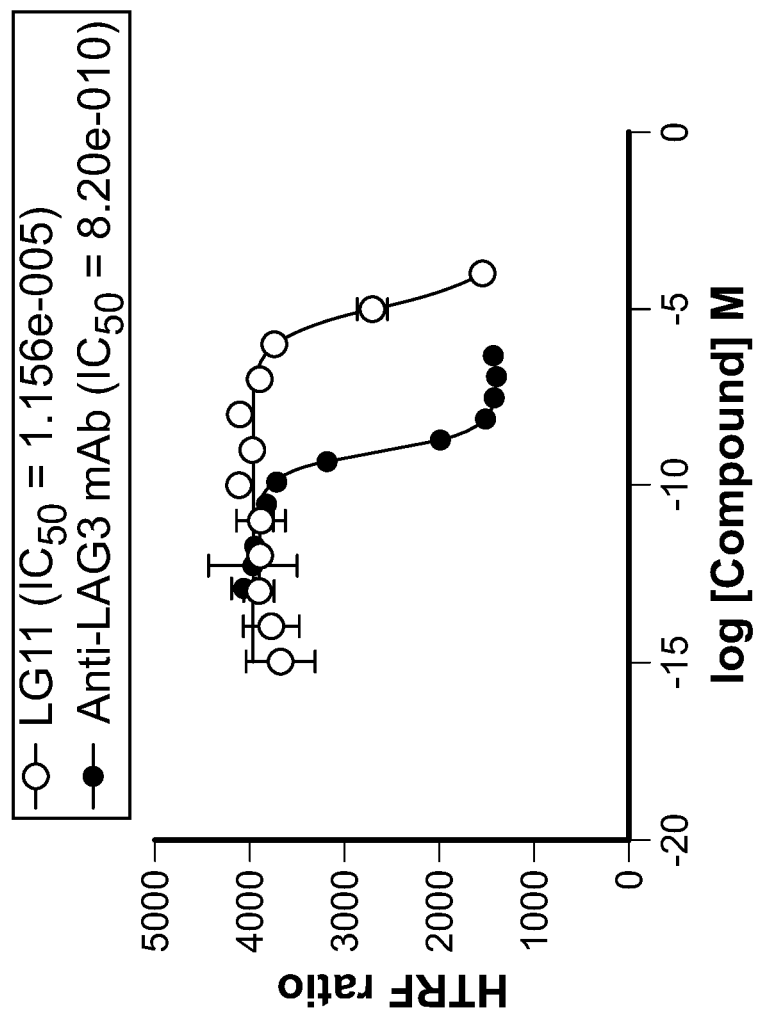
FIG. 3 is a graph showing the results of a TR-FRET assay testing peptide LG11 (SEQ ID NO:3).

Peptide LG11 (LAG3-11) showed a dose response with $IC_{50}$=1.156e-005 (FIG. 3).

Figures 4A, 4B:
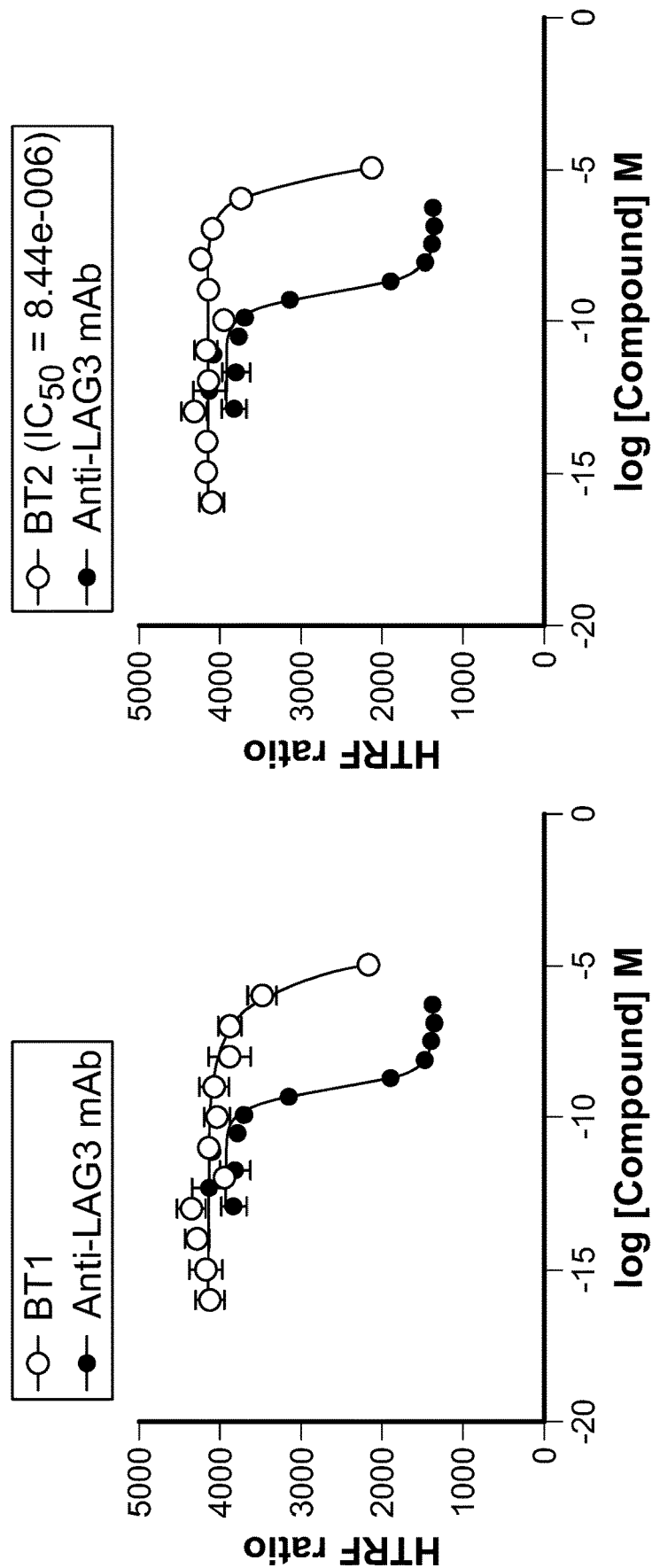
FIG. 4A is a graph showing the results of a TR-FRET assay testing peptide conjugate BT1.
FIG. 4B is a graph showing the results of a TR-FRET assay testing peptide conjugate BT2.

Peptide conjugates BT1 and BT2 were tested at 10-fold dilutions starting at 10 μM, because precipitation occurred at 100 μM. BT1 and BT2 ($IC_{50}$=8.44e-006) reduced the HTRF signal at 10 μM (FIG. 4A, FIG. 4B).

Figure 5:
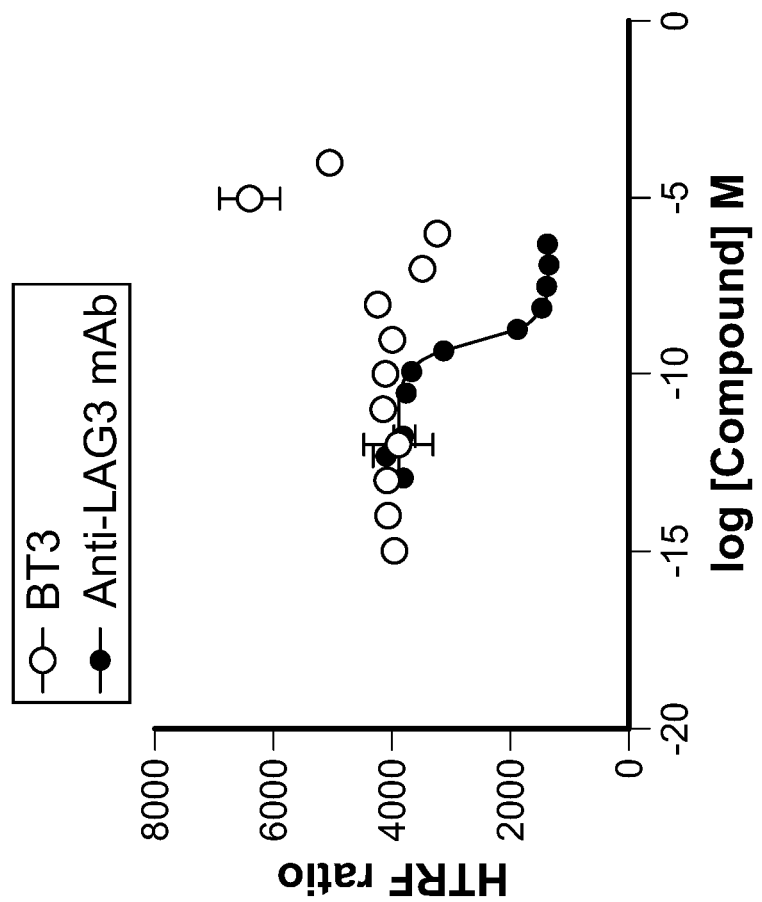
FIG. 5 is a graph showing the results of a TR-FRET assay testing peptide conjugate BT3.

Peptide conjugate BT3 was tested at 10-fold dilutions starting at 100 μM. BT3 demonstrated agonistic activity at 100 μM and 10 μM (FIG. 5).

Figure 6A:
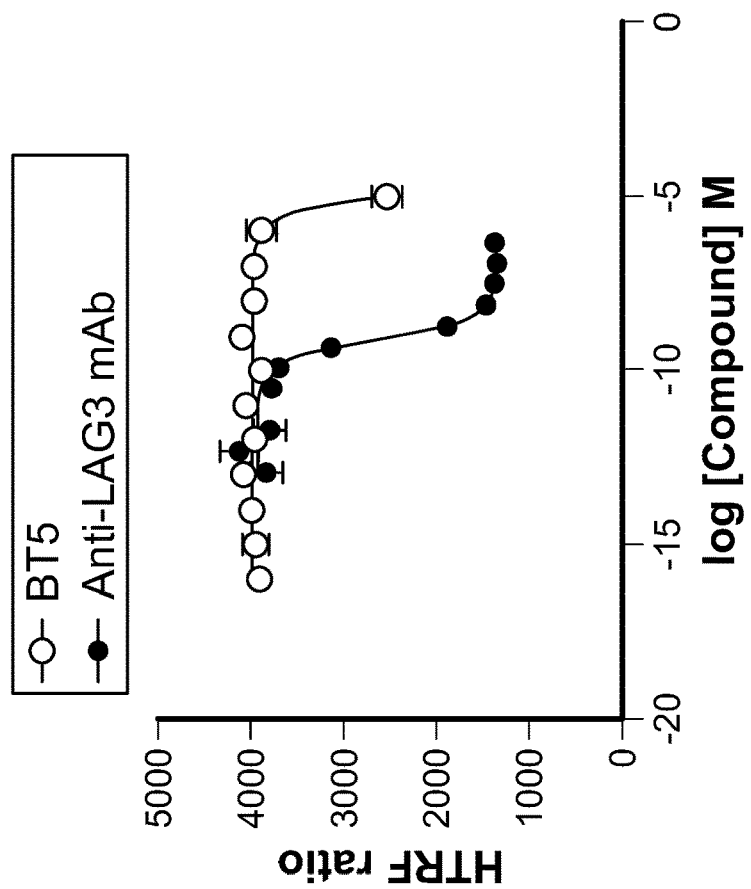
FIG. 6A is a graph showing the results of a TR-FRET assay testing peptide conjugate BT4.
Figure 6B:
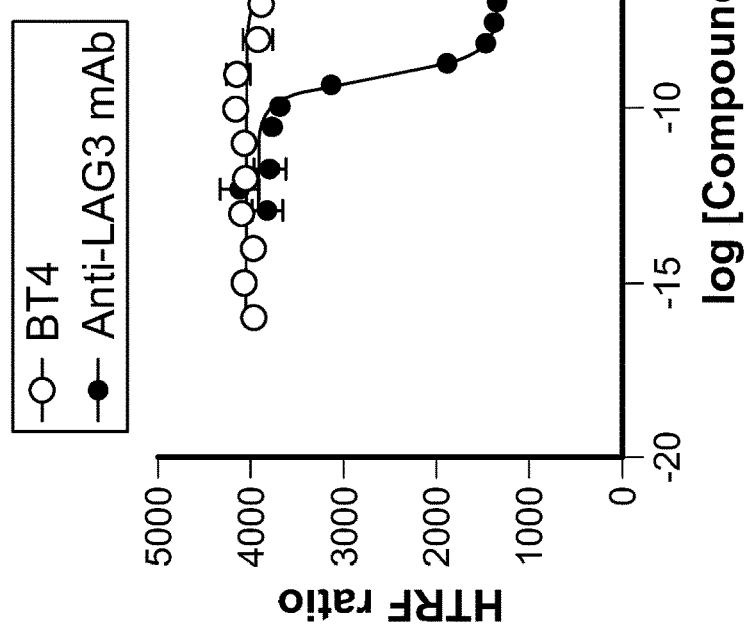
FIG. 6B is a graph showing the results of a TR-FRET assay testing peptide conjugate BT5.

Peptide conjugates BT4 and BT5 were tested at 10-fold dilutions starting at 10 μM, because precipitation occurred at 100 μM. BT4 and BT5 reduced the HTRF signal at 10 μM (FIG. 6A and FIG. 6B).

Figures 7A, 7B:
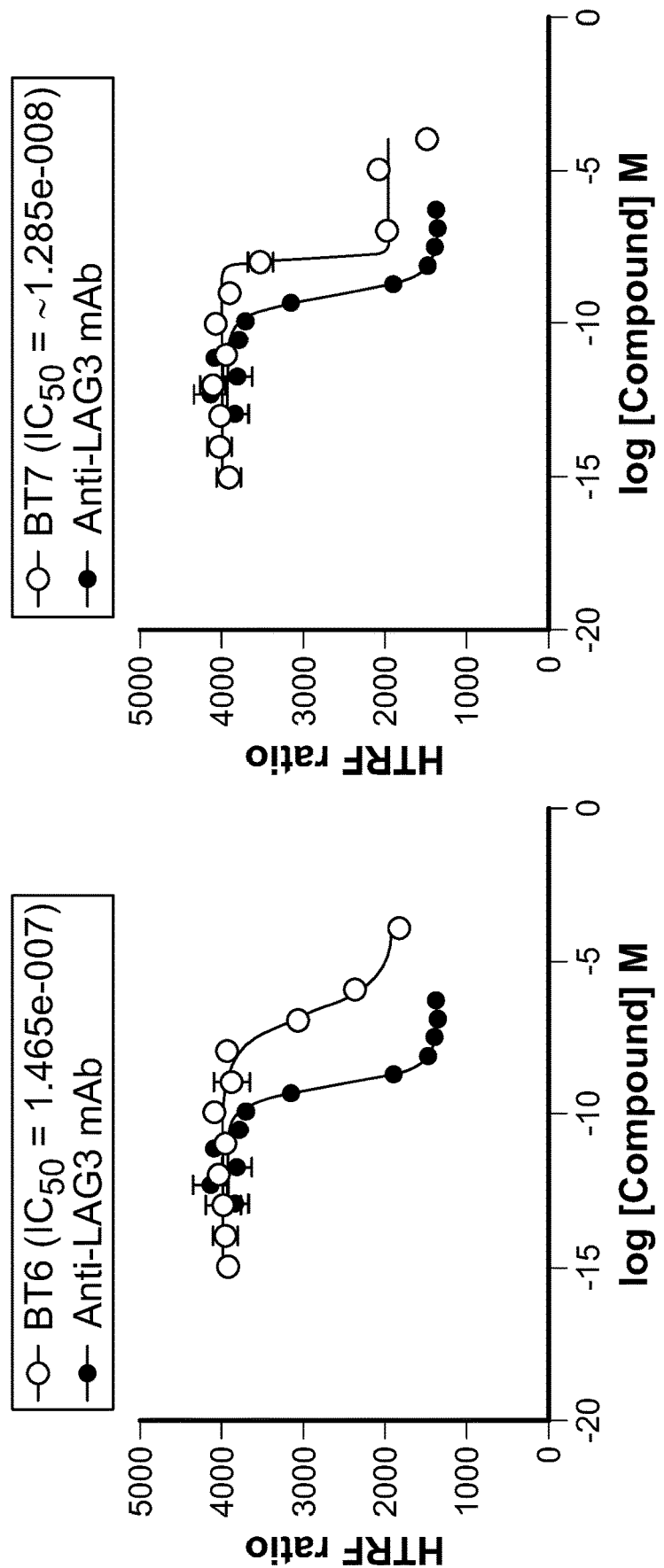
FIG. 7A is a graph showing the results of a TR-FRET assay testing peptide conjugate BT6.
FIG. 7B is a graph showing the results of a TR-FRET assay testing peptide conjugate BT7.

Peptide conjugates BT6 and BT7 were tested at 10-fold dilutions starting at 100 μM. BT4 ($IC_{50}$=1.4565e-007) and BT5 ($IC_{50}$=~1.285e-008) reduced the HTRF signal (FIG. 7A and FIG. 7B). The $IC_{50}$ for BT5 is an estimate due to the nature of the dose curve.

Figures 8A, 8B:
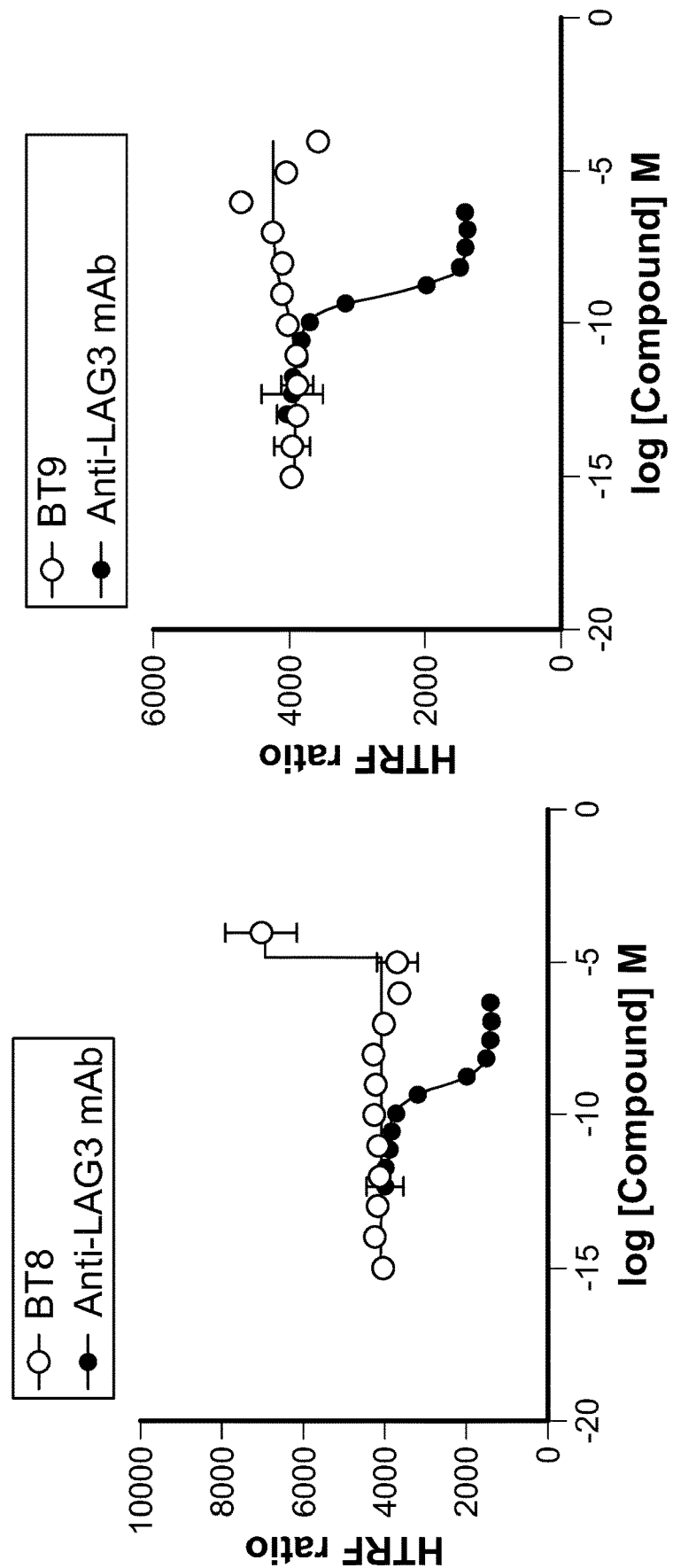
FIG. 8A is a graph showing the results of a TR-FRET assay testing peptide conjugate BT8.
FIG. 8B is a graph showing the results of a TR-FRET assay testing peptide conjugate BT9.

Peptide conjugates BT8 and BT9 were tested at 10-fold dilutions starting at 100 μM. BT8 showed agonistic activity at 100 μM (FIG. 8A), but no dose response was observed. BT9 showed no real effect (FIG. 8B).

Figure 9B:
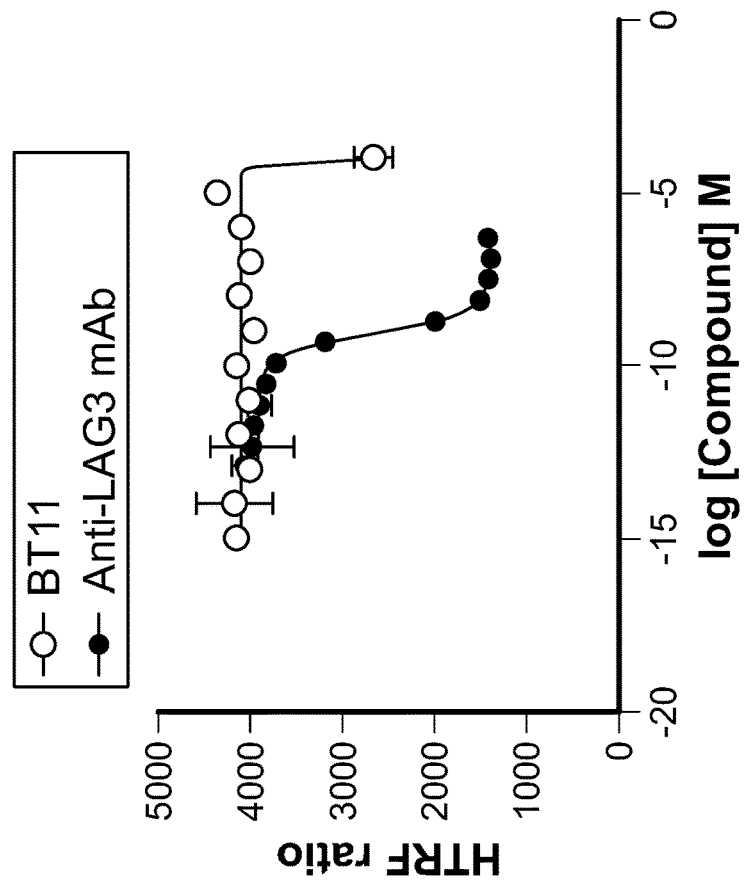
FIG. 9B is a graph showing the results of a TR-FRET assay testing peptide conjugate BT11.
Figure 9A:
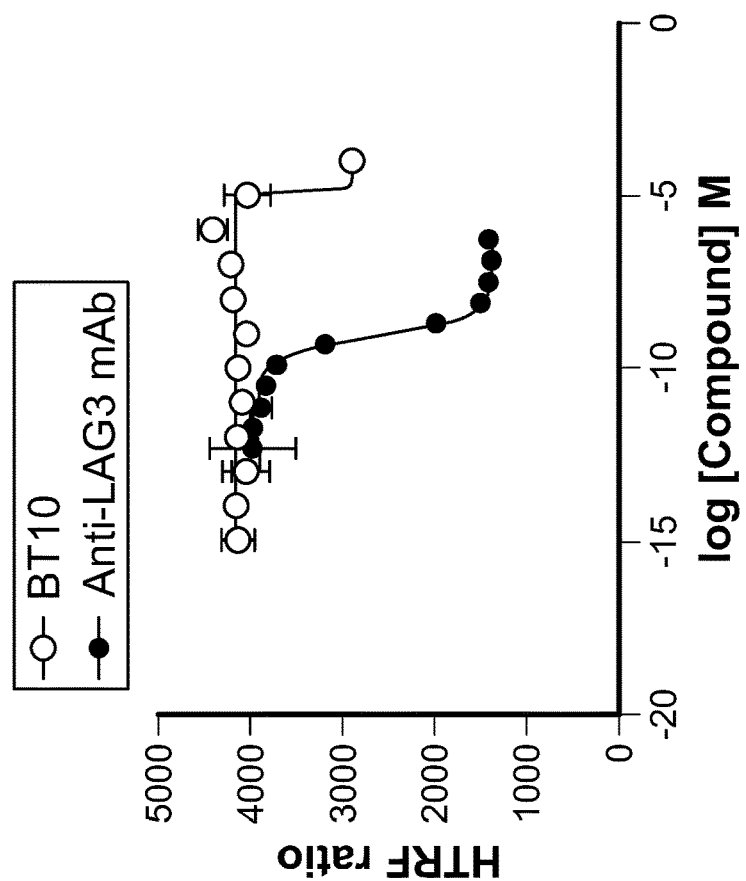
FIG. 9A is a graph showing the results of a TR-FRET assay testing peptide conjugate BT10.

Peptide conjugates BT10 and BT11 were tested at 10-fold dilutions starting at 100 μM. BT10 and BT11 showed activity at 100 μM; however no dose response was observed (FIG. 9A and FIG. 9B).

In summary, peptide conjugates BT1, BT2, BT4-7 all showed some level of antagonistic activity. $IC_{50}$ values were obtained for BT2, BT6 and BT7; these values were lower relative to the $IC_{50}$ for LG11; see Table 3.

TABLE 3

| Peptide or Peptide Conjugate | $IC_{50}$ |
|---|---|
| LG11 | 1.156e-005 |
| BT2 | 8.44e-006 |
| BT6 | 1.4565e-007 |
| BT7 | ~1.285e-008 (estimated) |

Peptide conjugates BT9, B10, and B11, which only contain LD10 sequences, showed no or activity only at 100 μM. The lack of a dose curve would suggest that the response at 100 μM may not accurately reflect the response at 100 μM.

While BT8 showed agonistic activity, it was only at 100 μM, suggesting it may not accurately reflect activity of BT8 at that concentration.

Example 3. Effect of Peptide Conjugates in a PD1/PDL1 Cell Reporter Assay

Jurkat cells expressing PD1 and SHP1 proteins, each fused to a fragment of enzyme fragment complementation (EFC) system, were co-incubated with PDL1-presenting U2OS cells. This results in PD1 activation and SHP1 recruitment to the PD1 receptors, bringing together the two EFC fragments and generating a light signal. Cells in co-culture were incubated at room temperature (RT) for 2 h (PD1 assay). The assay signal was generated using the PathHunter Bioassay Detection kit. Microplates were read following signal generation using a PerkinElmer ENVISION™ instrument for chemiluminescent signal detection. Inhibitory peptides or antibodies added to the culture result in reduction of light signal. The degree of inhibition was calculated using the following formula:

Percent inhibition=100%×[1−(mean RLU of test sample−mean RLU of vehicle control)/mean RLU of EC80 control−mean RLU of vehicle control)].

Peptide conjugates BT1-BT11 were tested at three concentrations: 3.6 μM, 10.8 μM, 32.5 μM in triplicate wells. peptide conjugates were dissolved in DMSO and serially diluted in assay buffer. The highest concentration that can be tested in this assay was 32.5 μM peptide conjugate (1% DMSO).

Peptides LD12 (SEQ ID NO:9), LD10 (SEQ ID NO:1), and LD16 (SEQ ID NO:10) were tested at three concentrations: 11 μM, 33 μM, 100 μM in triplicate. LD peptides were dissolved in water and serially diluted in assay buffer. RLUs were measured at the end of the assay, and % Inhibition (% Efficiency) was calculated using the formula above.

Figure 10:
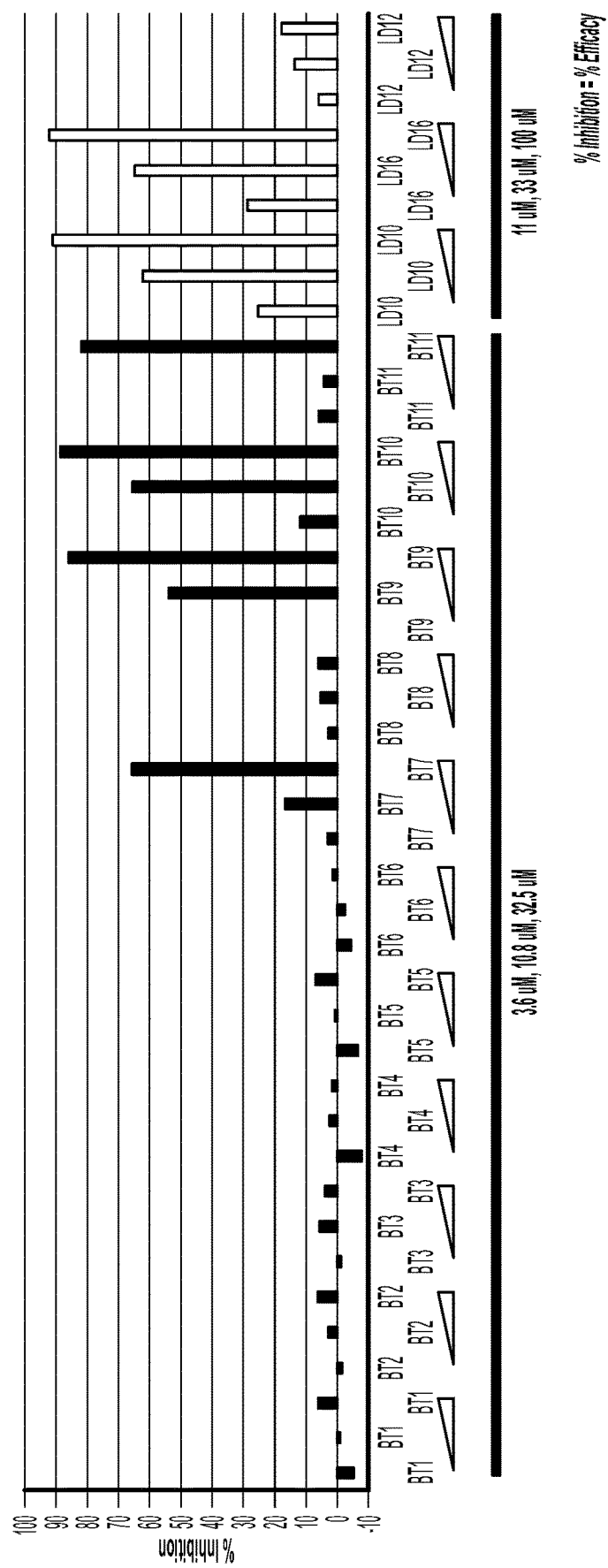
FIG. 10 is a graph showing the results of a PD1-PDL1 cell reporter assay testing various peptide conjugates and peptides.

The results are shown in FIG. 10.

The results showed that peptide conjugates BT7, BT9, BT10, and BT11 reduced the activity of PD1 at one or two of the tested concentrations. BT9, BT10, and BT11 each contain two LD10 peptides in different orientations, while peptide conjugate BT7 contains LD10 and LG11 sequences; see Table 2.

Peptide conjugates BT1, BT2, BT3, B4, BT5, BT6, and BT8 did not show inhibition at any of the tested concentrations.

Good dose-responses were obtained for positive control peptides LD10 and LD16, while negative control peptide LD12 did not show inhibition.

REFERENCES

Adams et al., "Big opportunities for small molecules in immuno-oncology," Nature Reviews Drug Discovery Advance Online Publication, Jul. 31, 2016, 20 pages Akinc et al., "A combinatorial library of lipid-like materials for delivery of RNAi therapeutics," Nat. Biotechnol. 26, 561-69, 2008

Akinc et al., "Development of lipidoid-siRNA formulations for systemic delivery to the liver," Mol. Ther. 17, 872-79, 2009

Alsaab et al., "PD1 and PD-L1 Checkpoint Signaling Inhibition for Cancer Immunotherapy: Mechanism, Combinations, and Clinical Outcome," Front. Pharmacol. 8, 561, 2017

Anderson et al., "semi-automated synthesis and screening of a large library of degradable cationic polymers for gene delivery," Angew. Chemi Int. Ed. 42, 3153-58, 2003

Andtbacka et al., "OPTiM: A randomized phase III trial of talimogene laherparepvec (T-VEC) versus subcutaneous (SC) granulocyte-macrophage colony-stimulating factor (GM-CSF) for the treatment (tx) of unresected stage IIIB/C and IV melanoma," J. Clin. Oncol. 31, abstract number LBA9008, 2013

Beavis et al., "Adenosine Receptor 2A Blockade Increases the Efficacy of Anti-PD1 through Enhanced Antitumor T-cell Responses," Cancer Immunol. Res. 3, 506-17, 2015

Behlke, "Chemical modification of siRNAs for in vivo use," Oligonucleotides. 2008; 18:305-19.

Behr, "The proton sponge: a trick to enter cells the viruses did not exploit," Int. J. Chem. 2, 34-36, 1997

Bensinger et al., "A phase 1 study of lucatumumab, a fully human anti-CD40 antagonist monoclonal antibody administered intravenously to patients with relapsed or refractory multiple myeloma," Br J Haematol. 159, 58-66, 2012.

Benson & Caligiuri, "Killer Immunoglobulin-like Receptors and Tumor Immunity," Cancer Immunol Res 2014; 2:99-104

Bodanszky et al., Peptide Synthesis, John Wiley and Sons, 2d ed. (1976)

Boussif et al., "A versatile vector for gene and oligonucleotide transfer into cells in culture and in vivo: polyethylenimine," Proc. Nat'l. Acad. Sci. (USA) 92, 7297-301, 1995

Bramsen et al., "A large-scale chemical modification screen identifies design rules to generate siRNAs with high activity, high stability and low toxicity," Nucleic Acids Res. 2009; 37:2867-81

Bruno et al., "Basics and recent advances in peptide and protein drug delivery," Ther. Deliv. 4, 1443-67, 2013

Bu et al., "Learning from PD1 Resistance: New Combination Strategies," Trends Mol. Med. 22, 448-51, 2016

Burnett & Rossi, "RNA-based Therapeutics-Current Progress and Future Prospects," Chem Biol. 19, 60-71, 2012

Cao, "Advances in Delivering Protein and Peptide Therapeutics," Pharmaceutical Technology 40, 22-24, Nov. 2, 2016

Chan & McFadden, "Oncolytic Poxviruses," Ann. Rev. Virol. 1, 119-41, 2014

Chen et al., "Rapid discovery of potent siRNA-containing lipid nanoparticles enabled by controlled microfluidic formulation," J. Am. Chem. Soc. 134, 6948-51, 2012

Cherkassky et al., "Human CAR T cells with cell-intrinsic PD1 checkpoint blockade resist tumor-mediated inhibition," J. Clin. Invest. 126, 3130-44, 2016

Chiu et al., "siRNA function in RNAi: a chemical modification analysis," RNA 2003; 9:1034-48.

Chong et al., "PD1 blockade modulates chimeric antigen receptor (CAR)-modified T cells: refueling the CAR," Blood. 129(8), 1039-41, 2017, published on-line Dec. 28, 2016

Chowdhury et al., "Combination therapy strategies for improving PD1 blockade efficacy: a new era in cancer immunotherapy," J. Int. Med. doi: 10.1111/joim.12708, Epub ahead of print, Oct. 26, 2017

Creative Biolabs User Manual, "TriCo-20™ Phage Display 20-mer Random Peptide Library," 14 pages, Aug. 4, 2009

Dahlman et al., "In vivo endothelial siRNA delivery using polymeric nanoparticles with low molecular weight," Nat. Nanotechnol. 9, 648-55, 2014

Dempke et al., "Second- and third-generation drugs for immuno-oncology treatment—The more the better?" Eur. J. Cancer 74, 55-72, March 2017

Desigaux et al., "Self-assembled lamellar complexes of siRNA with lipidic aminoglycoside derivatives promote efficient siRNA delivery and interference," Proc. Nat'l. Acad. Sci. (USA) 104, 16534-39, 2007

Differding, "AUNP-12—A Novel Peptide Therapeutic Targeting PD1 Immune Checkpoint Pathway for Cancer Immunotherapy—Structure Activity Relationships & Peptide/Peptidomimetic Analogs," available at differding.com/data/AUNP_12_A_novel_peptide_therapeutic_targeting_PD_1_immune_checkpoint_pathway_for_cancer_immunotherapy.pdf, Feb. 26, 2014

Dong et al., "Lipopeptide nanoparticles for potent and selective siRNA delivery in rodents and nonhuman primates," Proc. Nat'l. Acad. Sci. (USA) 111, 3955-60, 2014

Dosta et al., "Surface charge tunability as a powerful strategy to control electrostatic interaction for high efficiency silencing, using tailored oligopeptide-modified poly(beta-amino ester)s (PBAEs)," Acta Biomater. 20, 82-93, 2015

Duraiswamy et al., "Dual Blockade of PD1 and CTLA-4 Combined with Tumor Vaccine Effectively Restores T-Cell Rejection Function in Tumors," Cancer Res 73, 3591-603, 2013

Fenton et al., "Bioinspired alkenyl amino alcohol ionizable lipid materials for highly potent in vivo mRNA delivery," Adv. Mater. 28, 2939-43, 2016

Feridooni et al., "Noninvasive Strategies for Systemic Delivery of Therapeutic Proteins —Prospects and Challenges," Chapter 8 of Sezer, ed., Smart Drug Delivery System, available at http://www.intechopen.com/books/smart-drug-delivery-system, Feb. 10, 2016

Freeman et al., "Phase I/II trial of intravenous NDV-HUJ oncolytic virus in recurrent glioblastoma multiforme," Mol. Ther. 13, 221-28, 2006

Gao et al., "VISTA is an inhibitory immune checkpoint that is increased after ipilimumab therapy in patients with prostate cancer," Nature Med. 23, 551-55, 2017

Geevarghese et al., "Phase I/II Study of Oncolytic *Herpes Simplex* Virus NV1020 in Patients with Extensively Pre-treated Refractory Colorectal Cancer Metastatic to the Liver," Hum. Gene Ther. 21, 1119-28, 2010

Guo et al., "Systemic delivery of therapeutic small interfering RNA using a pH-triggered amphiphilic poly-L-lysinenanocarrier to suppress prostate cancer growth in mice," Eur. J. Pharm. Sci. 45, 521-32, 2012

Harvey et al., "Efficacy of anti-ICOS agonist monoclonal antibodies in preclinical tumor models provides a rationale for clinical development as cancer immunotherapeutics," Journal for ImmunoTherapy of Cancer 3(Suppl 2), O9, 2015

He et al., "Lymphocyte-activation gene-3, an important immune checkpoint in cancer," Cancer Sci. 107, 1193-97, 2016

Howard et al., "RNA interference in vitro and in vivo using a novel chitosan/siRNA nanoparticle system," Mol. Ther. 14, 476-84, 2006

Huard et al., "Cellular expression and tissue distribution of the human LAG-3-encoded protein, an MHC class II ligand," Immunogenetics 39 (3): 213-7, 1994

Huard et al., "CD4/major histocompatibility complex class II interaction analyzed with CD4- and lymphocyte activation gene-3 (LAG-3)-Ig fusion proteins," J. Immunol. 25, 2718-21, 1995

Huseni et al., "Anti-tumor efficacy and biomarker evaluation of agonistic anti-OX40 antibodies in preclinical models," Journal for ImmunoTherapy of Cancer 2(Suppl 3), P105, 2014

Infante et al., "A phase Ib dose escalation study of the OX40 agonist MOXR0916 and the PD-L1 inhibitor atezolizumab in patients with advanced solid tumors," J Clin Oncol. 34(suppl; abstr 101), 2016

John et al., "Blockade of PD1 immunosuppression boosts CAR T-cell therapy," OncoImmunology 2, e26286, 3 pages, 2013

Johnson et al., "A Cancer Research UK phase I study evaluating safety, tolerability, and biological effects of chimeric anti-CD40 monoclonal antibody (MAb), Chi Lob 7/4," J Clin Oncol. 28, 2507, 2010.

Johnson et al., "Clinical and Biological Effects of an Agonist Anti-CD40 Antibody: A Cancer Research UK Phase I Study," Clin Cancer Res 21, 1321-28, 2015

Judge & MacLachlan, "Overcoming the innate immune response to small interfering RNA," Hum Gene Ther. 2008; 19:111-24.

Kaczmarek et al., "Advances in the delivery of RNA therapeutics: from concept to clinical reality," Genome Medicine 2017; 9:60, 16 pages Kanasty et al., "Delivery materials for siRNA therapeutics," Nat. Mater. 12, 967-77, 2013

Kauffman et al., "Optimization of lipid nanoparticle formulations for mRNA delivery in vivo with fractional factorial and definitive screening designs," Nano Lett. 15, 7300-06, 2015

Kauffman et al., "Efficacy and immunogenicity of unmodified and pseudouridine-modified mRNA delivered systemically with lipid nanoparticles in vivo," Biomaterials. 2016; 109:78-87.

Kaufmann et al., "Chemovirotherapy of Malignant Melanoma with a Targeted and Armed Oncolytic Measles Virus," J. Invest. Dermatol. 133, 1034-42, 2013

Kavikansky & Pavlick, "Beyond Checkpoint Inhibitors: The Next Generation of Immunotherapy in Oncology," Amer. J. Hematol. Oncol. 13, 9-20, 2017

Khubchandani et al., "Dacetuzumab, a humanized mAb against CD40 for the treatment of hematological malignancies," Curr Opin Investig Drugs 10, 579-87, 2009.

Khuri et al., "A controlled trial of intratumoral ONYX-015, a selectively-replicating adenovirus, in combination with cisplatin and 5-fluorouracil in patients with recurrent head and neck cancer," Nat. Med. 6, 879-85, 2000

Kisielow et al., "Expression of lymphocyte activation gene 3 (LAG-3) on B cells is induced by T cells". European Journal of Immunology 35 (7): 2081-8, 2005

Kontermann, "Half-life extended biotherapeutics," Expert Opin. Biol. Ther. 16, 903-15, 2016.

Kozielski et al., "A bioreducible linear poly(β-amino ester) for siRNA delivery," Chem. Commun. (Camb). 49, 5319-21, 2013

Lawler et al., "Oncolytic Viruses in Cancer Treatment," JAMA Oncol. 3, 841-49, 2017 (published on-line Jul. 21, 2016)

Le Mercier et al., "VISTA Regulates the Development of Protective Antitumor Immunity," Cancer Res 2014; 74:1933-1944

Leone et al., "A2aR antagonists: Next generation checkpoint blockade for cancer immunotherapy," Computational and Structural Biotechnology Journal 13, 265-72, 2015

Leus et al., "VCAM-1 specific PEGylated SAINT-based lipoplexes deliver siRNA to activated endothelium in vivo but do not attenuate target gene expression," Int. J. Pharm. 469, 121-31, 2014

Li et al., "Discovery of peptide inhibitors targeting human programmed death 1 (PD1) receptor," Oncotarget 7, 64967-76, Aug. 12, 2016

Li et al., "Effects of chemically modified messenger RNA on protein expression," Bioconjug Chem. 2016; 27:849-53.

Liang, "Oncorine, the World First Oncolytic Virus Medicine and its Update in China," Curr. Cancer Drug Targets 18, 171-76, 2018

Lichtenegger et al., "Targeting LAG-3 and PD1 to Enhance T Cell Activation by Antigen-Presenting Cells," Front. Immunol. 9, 385, doi: 10.3389/fimmu.2018.00385.

Linch et al., "OX40 agonists and combination immunotherapy: putting the pedal to the metal," Frontiers in Oncology 5, 14 pages, 2015

Liu et al., "Immune-checkpoint proteins VISTA and PD1 nonredundantly regulate murine T-cell responses," Proc. Nat'l. Acad. Sci. USA 112, 6682-87, 2015

Lorence et al., "Phase 1 clinical experience using intravenous administration of PV701, an oncolytic Newcastle disease virus," Curr. Cancer Drug Targets 7, 157-67, 2007

Lorenz et al., "Steroid and lipid conjugates of siRNAs to enhance cellular uptake and gene silencing in liver cells," Bioorganic Med. Chem. Lett. 14, 4975-77, 2004

Love et al., "Lipid-like materials for low-dose, in vivo gene silencing," Proc. Nat'l. Acad. Sci. (USA) 107, 1864-69, 2010

Lu et al., "Replicating retroviral vectors for oncolytic virotherapy of experimental hepatocellular carcinoma," Oncol. Rep. 28, 21-26, 2012

Lundstrom, "Oncolytic Alphaviruses in Cancer Immunotherapy," Vaccines 5, pages 1-17, 2017

Lynn & Langer, "Degradable poly(β-amino esters): synthesis, characterization, and self-assembly with plasmid DNA," J. Am. Chem. Soc. 122, 10761-18, 2000

Magiera-Mularz et al., "Bioactive macrocyclic inhibitors of the PD1/PD-L1 immune checkpoint," Angewandte Chemie Int. Ed. 10.1002/anie.201707707, e-published Sep. 26, 2017

Mao et al., "Pathological α-synuclein transmission initiated by binding lymphocyte-activation gene 3," Science 353, aah3374, 2016

Maute et al., "Engineering high-affinity PD1 variants for optimized immunotherapy and immuno-PET imaging," Proc. Natl. Acad. Sci. USA, E6506-E6514, published online Nov. 10, 2015

McDonald et al., "A measles virus vaccine strain derivative as a novel oncolytic agent against breast cancer," Breast Cancer Treat. 99, 177-84, 2006

McOmie, Protective Groups in Organic Chemistry, Plenum Press, New York, N.Y., 1973

Mediavilla-Varela et al., "A Novel Antagonist of the Immune Checkpoint Protein Adenosine A2a Receptor Restores Tumor-Infiltrating Lymphocyte Activity in the Context of the Tumor Microenvironment," Neoplasia 19, 530-36, 2017

Mellemgaard et al., "Combination immunotherapy with IDO vaccine and PD1 inhibitors in advances HSCLC," DOI: 10.1200/JCO.2017.35.15_suppl.TPS2610 Journal of Clinical Oncology 35, no. 15_suppl—published online before print, 2017

Merrifield, "Solid phase peptide synthesis I: Synthesis of a tetrapeptide," J. Am. Chem. Soc. 85:2149-54, 1963

Messenheimer et al., "Timing of PD1 Blockade Is Critical to Effective Combination Immunotherapy with Anti-OX40," Clin. Cancer Res. 23, DOI: 10.1158/1078-0432.CCR-16-2677 Published October 2017

Michaelson et al., "Preclinical evaluation of JTX-2011, an anti-ICOS agonist antibody,", Abstract 573, Proceedings: AACR 107th Annual Meeting 2016; Apr. 16-20, 2016; New Orleans, La.

Morrissey et al., "Immunotherapy and Novel Combinations in Oncology: Current Landscape, Challenges, and Opportunities," Clinical and Translational Science 9, 89-104, 2016

Morrissey et al., "Potent and persistent in vivo anti-HBV activity of chemically modified siRNAs," Nat. Biotechnol. 23, 1002-07, 2005

Moschos et al., "Lung delivery studies using siRNA conjugated to TAT(48-60) and penetratin reveal peptide induced reduction in gene expression and induction of innate immunity," Bioconjug. Chem. 18, 1450-59, 2007

Nair et al., "Multivalent N-acetylgalactosamine-conjugated siRNA localizes in hepatocytes and elicits robust RNAi-mediated gene silencing," J. Am. Chem. Soc. 136, 16958-61, 2014

Neurath et al., eds., The Proteins, Vol. II, 3d ed., pp. 105-237, Academic Press, New York, N.Y. (1976)

Nishina et al., "Efficient in vivo delivery of siRNA to the liver by conjugation of alphatocopherol," Mol. Ther. 16, 734-40, 2008

Ott et al., "Combination immunotherapy: a road map," J. ImmunoTherapy of Cancer 5, 16, 2017

Pack et al., "Design and development of polymers for gene delivery," Nat. Rev. Drug discov. 4, 581-93, 2005

Patel et al., "Recent Advances in Protein and Peptide Drug Delivery: A Special Emphasis on Polymeric Nanoparticles," Protein. Pept. Lett. 21, 1102-20, 2014

Patil et al., "Targeting Immune Cell Checkpoints During Sepsis," Int. J. Mol. Sci. 18, 2413, 2017.

Penchala et al., "A biomimetic approach for enhancing the in vivo half-life of peptides," Nat. Chem. Biol. 11, 793-98, 2015

Phuangsab et al., "Newcastle disease virus therapy of human tumor xenografts: antitumor effects of local or systemic administration," Cancer Lett. 172, 27-36, 2001

Prakash et al., "Positional effect of chemical modifications on short interference RNA activity in mammalian cells," J Med Chem. 2005; 48:4247-53

Pratt & MacRae, "The RNA-induced silencing complex: a versatile gene-silencing machine," J Biol Chem. 2009; 284:17897-901

Rehman et al., "Mechanism of polyplex- and lipoplexme-diated delivery of nucleic acids: real-time visualization of transient membrane destabilization without endosomal lysis," ACS Nano. 7, 3767-77, 2013

Rivera et al., "Hair Repigmentation During Immunotherapy Treatment With an Anti-Programmed Cell Death 1 and Anti-Programmed Cell Death Ligand 1 Agent for Lung Cancer," JAMA Dermatol. 153, 1162-65, 2017

Rodriguez et al., "Design and implementation of a high yield production system for recombinant expression of peptides," Microbial Cell Factories 13, 65, 10 pages, 2014

Rudin et al., "Phase I clinical study of Seneca Valley Virus (SVV-001), a replication-competent picornavirus, in advanced solid tumors with neuroendocrine features," Clin. Cancer Res. 17, 888-95, 2011

Sahin et al., "mRNA-based therapeutics—developing a new class of drugs," Nat Rev Drug Discov. 2014; 13:759-80

Sakuishi et al., "Targeting Tim-3 and PD1 pathways to reverse T cell exhaustion and restore anti-tumor immunity," J. Exp. Med. 20, 2187-94, 2010

Schaer et al., "Modulation of GITR for cancer immunotherapy," Curr Opin Immunol. 24, 217-24, 2012

Schroeder et al., "Lipid-based nanotherapeutics for siRNA delivery," J. Int. Med. 267, 9-21, 2010

Sharma & Allison, "Immune Checkpoint Targeting in Cancer Therapy: Toward Combination Strategies with Curative Potential," Cell 161, 205-14, 2015

Shindo et al., "Combination Immunotherapy with 4-1BB Activation and PD1 Blockade Enhances Antitumor Efficacy in a Mouse Model of Subcutaneous Tumor," Anticancer Res. 35, 129-36, 2015

Shrimali et al., "Concurrent PD1 Blockade Negates the Effects of OX40 Agonist Antibody in Combination Immunotherapy through Inducing T-cell Apoptosis," Cancer Immunol Res 5(9), pages OF1-12, Aug. 28, 2017

Skalniak et al., "Small-molecule inhibitors of PD1/PD-L1 immune checkpoint alleviate the PD-L1-induced exhaustion of T-cells," Oncotarget, Advance Publications, Aug. 7, 2017, 15 pages Smith, "Pigmented skin lesions lightened during melanoma immunotherapy," http://www.mdedge.com/edermatologynews/article/132598/melanoma/pigmented-skin-lesions-lightened-during-melanoma, Mar. 2, 2017

Soutschek et al., "Therapeutic silencing of an endogenous gene by systemic administration of modified siRNAs," Nature. 2004; 432:173-78

Spodzieja et al., "Design of short peptides to block BTLA/HVEM interactions for promoting anticancer T-cell responses," PLoS ONE 12(6): e0179201, 17 pages, 2017

Stojdl et al., "Exploiting tumor-specific defects in the interferon pathway with a previously unknown oncolytic virus," Nat. Med. 6, 821-25, 2000

Stojdl et al., "VSV strains with defects in their ability to shutdown innate immunity are potent systemic anti-cancer agents," Cancer Cell 4, 263-75, 2003

Stuart & Young, Solid Phase Peptide Synthesis, Pierce Chemical Company, Rockford, Ill., 1984

Tigue et al., "MEDI1873, a potent, stabilized hexameric agonist of human GITR with regulatory T-cell targeting potential," ONCOIMMUNOLOGY 6(3), e1280645 (14 pages), Feb. 3, 2017

Triebel et al., "LAG3, a novel lymphocyte activation gene closely related to CD4," J. Exp. Med. 171, 1393-405, 1990

Tsutsumi et al., "Evaluation of polyamidoamine dendrimer/alpha-cyclodextrin conjugate (generation 3, G3) as a novel carrier for small interfering RNA (siRNA)," J. Control. Release 119, 349-59, 2007

Tuck, "Development of Small Molecule Checkpoint Inhibitors," Immune Checkpoint Inhibitors Symposium, 28 pages, Mar. 14-16, 2017

Tzeng et al., "Cystamine-terminated poly(beta-amino ester)s for siRNA delivery to human mesenchymal stem cells and enhancement of osteogenic differentiation," Biomaterials 33, 8142-51, 2012

Tzeng et al., "PD1 blockage reverses immune dysfunction and *hepatitis* B viral persistence in a mouse animal model," PLoS One 7(6):e39179, 2012

Van Dessel et al., "Potent and tumor specific: arming bacteria with therapeutic proteins," Ther. Deliv. 6, 385-99, 2015

Vonderheide and Glennie, "Agonistic CD40 antibodies and cancer therapy," Clin. Cancer Res. 19, 1035-43, 2013

Vonderheide et al., "Clinical activity and immune modulation in cancer patients treated with CP-870,893, a novel CD40 agonist monoclonal antibody," J Clin Oncol. 25, 876-83, 2007

Wang et al., "Anaplastic lymphoma kinase (ALK) inhibitors: a review of design and discovery," Med. Chem. Commun. 5, 1266-79, 2014

Wang et al., "VISTA, a novel mouse Ig superfamily ligand that negatively regulates T cell responses," J. Exp. Med. 208, 577-92, 2011

Wang et al., "Fibrinogen-like Protein 1 is a Major Immune Inhibitory Ligand of LAG-3," Cell 176, 334-47, 2019

Wittrup & Lieberman, "Knocking down disease: a progress report on siRNA therapeutics," Nat Rev Genet. 2015; 16:543-52

Won et al., "Missing pieces in understanding the intracellular trafficking of polycation/DNA complexes," J. Control. Release 139, 88-93, 2009

Workman et al., "LAG-3 regulates plasmacytoid dendritic cell homeostasis," Journal of Immunology 182 (4): 1885-91, 2009

Xia et al., "Antibody-mediated targeting of siRNA via the human insulin receptor using avidin—biotin technology," Mol. Pharm. 6, 747-51, 2009

Yang et al., "Oral vaccination with salmonella simultaneously expressing Yersinia pestis F1 and V antigens protects against bubonic and pneumonic plague," J Immunol. 178, 1059-67, 2007
Ye et al., "T-cell exhaustion in chronic *hepatitis* B infection: current knowledge and clinical significance," Cell Death Dis. 19, e1694, 2015
Young et al., "Co-inhibition of CD73 and A2AR Adenosine Signaling Improves Anti-tumor Immune Responses," Cancer Cell 30, 391-403, 2016
Yu et al., "Disposition and pharmacology of a GalNAc3-conjugated ASO targeting human lipoprotein(a) in mice," Mol. Ther. Nucleic Acids 5, e317, 2016
Zarganes-Tzitzikas et al., "Inhibitors of programmed cell death 1 (PD1): a patent review," Expert Opinion on Therapeutic Patents 26, 973-77, published on-line Jul. 6, 2016
Zhan et al., "From monoclonal antibodies to small molecules: the development of inhibitors targeting the PD1/PD-L1 pathway," Drug Discovery Today 21, 1027-36, June 2016
Zorzi et al., "Acylated heptapeptide binds albumin with high affinity and application as tag furnishes long-acting peptides," Nature Communications 8, 16092, 2017

The invention claimed is:

1. A compound comprising (a) a first peptide, (b) a PEG linker covalently attached to the C terminus of the first peptide, and (c) a second peptide covalently attached to the PEG linker at the N terminus of the second peptide, wherein:
   (i) the first peptide has the amino acid sequence SEQ ID NO:1 and the second peptide has an amino acid sequence selected from the group consisting of SEQ ID NO:1, SEQ ID NO:2, SEQ ID NO:3, and SEQ ID NO:4;
   (ii) the first peptide has the amino acid sequence SEQ ID NO:2 and the second peptide has an amino acid sequence selected from the group consisting of SEQ ID NO:1, SEQ ID NO:2, and SEQ ID NO:3;
   (iii) the first peptide has the amino acid sequence SEQ ID NO:3 and the second peptide has an amino acid sequence selected from the group consisting of SEQ ID NO:1 and SEQ ID NO:2; or
   (iv) the first peptide has the amino acid sequence SEQ ID NO:4 and the second peptide has an amino acid sequence selected from the group consisting of SEQ ID NO:1 and SEQ ID NO:2.

2. The compound of claim 1, wherein the first peptide comprises an N-terminal modification.

3. The compound of claim 1, wherein the second peptide comprises a C terminal modification.

4. The compound of claim 1, wherein the first peptide has the amino acid sequence SEQ ID NO:1, wherein the first peptide contains D-serine at its N terminus.

5. The compound of claim 1, wherein the second peptide has the amino acid sequence SEQ ID NO:1, wherein the second peptide contains D-serine at its N terminus.

6. The compound of claim 1, wherein:
   (i) the first peptide has the amino acid sequence SEQ ID NO:1 and the second peptide has the amino acid sequence SEQ ID NO:3;
   (ii) the first peptide has the amino acid sequence SEQ ID NO:3 and the second peptide has an amino acid sequence selected from the group consisting of SEQ ID NO:1 and SEQ ID NO:2;
   (iii) the first peptide has the amino acid sequence SEQ ID NO:4 and the second peptide has the amino acid sequence SEQ ID NO:2; or
   (iv) the first peptide has the amino acid sequence SEQ ID NO:2 and the second peptide has an amino acid sequence selected from the group consisting of SEQ ID NO:3 and SEQ ID NO:4.

7. The compound of claim 1, wherein:
   (i) the first peptide has the amino acid sequence SEQ ID NO:2 and the second peptide has the amino acid sequence SEQ ID NO:3;
   (ii) the first peptide has the amino acid sequence SEQ ID NO:1 and the second peptide has an amino acid sequence selected from the group consisting of SEQ ID NO:1 and SEQ ID NO:2; or
   (iii) the first peptide has the amino acid sequence SEQ ID NO:2 and the second peptide has the amino acid sequence SEQ ID NO:1.

8. A pharmaceutical composition comprising:
   (a) a compound of claim 1; and
   (b) a pharmaceutically acceptable carrier.

9. A method of inhibiting the progression of a hyperproliferative disorder, inhibiting the progression of sepsis, inhibiting the progression of an infectious disease, enhancing a response to a vaccine, or inhibiting the progression of a synucleinopathy, comprising administering to an individual in need thereof an effective amount of a compound according to claim 1.

10. The method of claim 9, wherein the pharmaceutical composition is administered to inhibit progression of the hyperproliferative disorder.

11. The method of claim 10, wherein the hyperproliferative disorder is a cancer.

12. The method of claim 9, wherein the compound is administered to inhibit the progression of sepsis.

13. The method of claim 9, wherein the compound is administered to inhibit the progression of an infectious disease.

14. The method of claim 9, wherein the compound is administered to enhance a response to a vaccine.

15. The method of claim 9, wherein the compound is administered to inhibit the progression of a synucleinopathy, wherein the compound is a compound comprising, (a) a first peptide, (b) a PEG linker covalently attached to the C terminus of the first peptide, and (c) a second peptide covalently attached to the PEG linker at the N terminus of the second peptide, wherein: (i) the first peptide has the amino acid sequence SEQ ID NO:1 and the second peptide has the amino acid sequence SEQ ID NO:3; (ii) the first peptide has the amino acid sequence SEQ ID NO:3 and the second peptide has the amino acid sequence selected from the group consisting of SEQ ID NO:1 and SEQ ID NO:2; (iii) first peptide has the amino acid sequence SEQ ID NO:4 and the second peptide has the amino acid sequence SEQ NO:2; or (iv) the first peptide has the amino acid sequence SEQ ID NO:2 and the second peptide has an amino acid sequence selected from the group consisting of SEQ ID NO:3 and SEQ ID NO:4.

16. The method of claim 15, wherein the synucleinopathy is selected from the group consisting of Parkinson's disease (PD), dementia with Lewy bodies (DLB), pure autonomic failure (PAF), and multiple system atrophy (MSA).

* * * * *

```
                                SEQUENCE LISTING

<160> NUMBER OF SEQ ID NOS: 10

<210> SEQ ID NO 1
<211> LENGTH: 18
<212> TYPE: PRT
<213> ORGANISM: Artificial Sequence
<220> FEATURE:
<223> OTHER INFORMATION: LD10 peptide, forward orientation

<400> SEQUENCE: 1

Ser Thr Gly Gln Ile Ser Thr Leu Arg Val Asn Ile Thr Ala Pro Leu
1               5                   10                  15

Ser Gln

<210> SEQ ID NO 2
<211> LENGTH: 18
<212> TYPE: PRT
<213> ORGANISM: Artificial Sequence
<220> FEATURE:
<223> OTHER INFORMATION: LD10 peptide, reverse orientation

<400> SEQUENCE: 2

Gln Ser Leu Pro Ala Thr Ile Asn Val Arg Leu Thr Ser Ile Gln Gly
1               5                   10                  15

Thr Ser

<210> SEQ ID NO 3
<211> LENGTH: 20
<212> TYPE: PRT
<213> ORGANISM: Artificial Sequence
```

```
<220> FEATURE:
<223> OTHER INFORMATION: LD11 peptide, forward orientation

<400> SEQUENCE: 3

Ser Ala Pro Trp Glu Pro Leu His Trp Pro Glu Asp Trp Trp Gln Gly
1               5                   10                  15

Thr Gly Glu Trp
            20

<210> SEQ ID NO 4
<211> LENGTH: 20
<212> TYPE: PRT
<213> ORGANISM: Artificial Sequence
<220> FEATURE:
<223> OTHER INFORMATION: LD11 peptide, reverse orientation

<400> SEQUENCE: 4

Trp Glu Gly Thr Gly Gln Trp Trp Asp Glu Pro Trp His Leu Pro Glu
1               5                   10                  15

Trp Pro Ala Ser
            20

<210> SEQ ID NO 5
<211> LENGTH: 21
<212> TYPE: PRT
<213> ORGANISM: Artificial Sequence
<220> FEATURE:
<223> OTHER INFORMATION: LAG3-56 peptide

<400> SEQUENCE: 5

His Ile Gln Asn Trp Ser Tyr Trp Leu Asn Gln Asp Met Met Asn Gln
1               5                   10                  15

Gln Val Trp Lys Ser
            20

<210> SEQ ID NO 6
<211> LENGTH: 20
<212> TYPE: PRT
<213> ORGANISM: Artificial Sequence
<220> FEATURE:
<223> OTHER INFORMATION: LAG3-42 peptide

<400> SEQUENCE: 6

Asp Trp Asn Phe Gln Gln Trp Asp Trp Lys Lys His Asn His Leu Asp
1               5                   10                  15

Ser His Val Val
            20

<210> SEQ ID NO 7
<211> LENGTH: 8
<212> TYPE: PRT
<213> ORGANISM: Mus musculus

<400> SEQUENCE: 7

Ser Ile Ile Asn Phe Glu Lys Leu
1               5

<210> SEQ ID NO 8
<211> LENGTH: 18
<212> TYPE: PRT
<213> ORGANISM: Artificial Sequence
<220> FEATURE:
<223> OTHER INFORMATION: LD10da peptide
<221> NAME/KEY: AMIDATION
<222> LOCATION: (18)...(18)
```

```
<223> OTHER INFORMATION: D-amino acid

<400> SEQUENCE: 8

Ser Thr Gly Gln Ile Ser Thr Leu Arg Val Asn Ile Thr Ala Pro Leu
1               5                   10                  15
Ser Gln

<210> SEQ ID NO 9
<211> LENGTH: 22
<212> TYPE: PRT
<213> ORGANISM: Artificial Sequence
<220> FEATURE:
<223> OTHER INFORMATION: LD12 peptide

<400> SEQUENCE: 9

Cys Arg Arg Thr Ser Thr Gly Gln Ile Ser Thr Ala Arg Val Asn Ile
1               5                   10                  15
Thr Ala Pro Leu Ser Gln
            20

<210> SEQ ID NO 10
<211> LENGTH: 19
<212> TYPE: PRT
<213> ORGANISM: Artificial Sequence
<220> FEATURE:
<223> OTHER INFORMATION: LD16 peptide

<400> SEQUENCE: 10

Thr Ser Thr Gly Gln Ile Ser Thr Leu Arg Val Asn Ile Thr Ala Pro
1               5                   10                  15
Leu Ser Gln
```